United States Patent [19]
Baker et al.

[11] Patent Number: 5,242,930
[45] Date of Patent: Sep. 7, 1993

[54] AZABICYCLIC COMPOUNDS, PHARMACEUTICAL COMPOSITIONS CONTAINING THEM AND THEIR USE IN THERAPY

[75] Inventors: Raymond Baker; Eileen M. Seward, both of Hertfordshire; Christopher Swain, Cambridge, all of England

[73] Assignee: Merck Sharp & Dohme Ltd., Hoddesdon

[21] Appl. No.: 830,822

[22] Filed: Feb. 4, 1992

[30] Foreign Application Priority Data

| Feb. 11, 1991 | [GB] | United Kingdom | 9102809 |
| Apr. 9, 1991 | [GB] | United Kingdom | 9107403 |
| Jun. 27, 1991 | [GB] | United Kingdom | 9113892 |
| Jul. 5, 1991 | [GB] | United Kingdom | 9114553 |

[51] Int. Cl.$^5$ ............... C07D 453/02; A61K 31/445
[52] U.S. Cl. ............................. 514/305; 546/137
[58] Field of Search ...................... 546/137; 514/305

[56] References Cited

U.S. PATENT DOCUMENTS

| 3,506,673 | 4/1970 | Warawa et al. | 546/137 |
| 3,796,714 | 3/1974 | Brack | 546/137 |
| 4,013,667 | 3/1977 | Yen | 546/137 |
| 4,013,668 | 3/1977 | Adelstein et al. | 546/137 |
| 4,125,531 | 11/1978 | Yen | 546/137 |
| 4,599,344 | 7/1986 | Morgan, Jr. | 546/137 |

FOREIGN PATENT DOCUMENTS

WO90/05729 5/1990 European Pat. Off.
86/05729 5/1990 World Int. Prop. O.

OTHER PUBLICATIONS

B. E. B. Sandberg et al, J. Med. Chem., 25, 1009 (1982).
Levine, et al Science, 226, pp. 547-549 (1984).
Mantyh, et al. Neuroscience, 25, (3), 817-837 (1988).
O'Byrne, et al Arthritis and Rheumatism, 33, 1023-8 (1990).
Hamel, et al, Can. J. Pharmacol. Physiol. 66, 1361-7 (1988).
Lotz, et al., Science 241, 1218-21 (1988).
Kimball, et al., J. Immunol., 141, (10), 3564-9 (1988).
Mantyh, et al PNAS, 85, 3235-9 (1988).
Yankner, et al, Science, 250, 279-82 (1990).
Warawa J. Med. Chem., 17, 497 (1974).
Warawa J. Med. Chem., 18 587 (1975).

*Primary Examiner*—Marianne M. Cintins
*Assistant Examiner*—Catherine S. Kilby Scalzo
*Attorney, Agent, or Firm*—Robert J. North; Joseph F. DiPrima

[57] ABSTRACT

Compounds of formula (I), and salts and prodrugs thereof

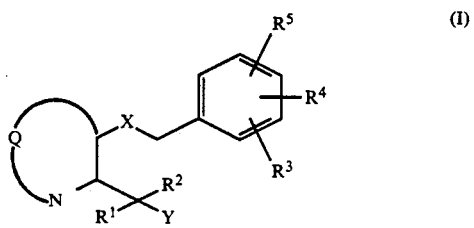

wherein

Q is the residue of an optionally substituted azabicyclic ring system;

X represents oxa or thia;

Y represents H or hydroxy;

$R^1$ and $R^2$ independently represent phenyl or thienyl, either of which groups may be optionally substituted by halo or trifluoromethyl;

$R^3$, $R^4$ and $R^5$ independently represent H, $C_{1-6}$ alkyl, $C_{2-6}$ alkenyl, $C_{2-6}$ alkynyl, halo, cyano, nitro, trifluoromethyl, trimethylsilyl, $-OR^a$, $SCH_3$, $SOCH_3$, $SO_2CH_3$, $-NR^aR^b$, $-NR^aCOR^b$, $-NR^aCO_2R^b$, $-CO_2R^a$ or $-CONR^aR^b$;

$R^a$ and $R^b$ independently represent H, $C_{1-6}$ alkyl, phenyl or trifluoromethyl, are tachykinin antagonists. They and compositions thereof are therefore useful in therapy.

11 Claims, No Drawings

AZABICYCLIC COMPOUNDS, PHARMACEUTICAL COMPOSITIONS CONTAINING THEM AND THEIR USE IN THERAPY

This invention relates to a class of azabicyclic compounds, which are useful as tachykinin antagonists. More particularly, the compounds of the invention comprise an azabicyclic ring system substituted by an arylmethyloxy or arylmethylthio moiety and by a benzhydryl, or like, moiety.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P:
Arg-Pro-Lys-Pro-Gln-Gln-Phe-Phe-Gly-Leu-Met-$NH_2$
Neurokinin A:
His-Lys-Thr-Asp-Ser-Phe-Val-Gly-Leu-Met-$NH_2$
Neurokinin B:
Asp-Met-His-Asp-Phe-Phe-Val-Gly-Leu-Met-$NH_2$ For example, substance P is believed inter alia to be involved in the neurotransmission of pain sensations [Otsuka et al. "Role of Substance P as a Sensory Transmitter in Spinal Cord and Sympathetic Ganglia" in 1982 Substance P in the Nervous System, Ciba Foundation Symposium 91, 13-34 (published by Pitman) and Otsuka and Yanagisawa, "Does Substance P Act as a Pain Transmitter?" TIPS (Dec. 1987) 8 506-510], specifically in the transmission of pain in migraine (B. E. B. Sandberg et al. J. Med Chem, (1982) 25 1009) and in arthritis [Levine et al in Science (1984) 226 547–549]. These peptides have also been implicated in gastrointestinal (GI) disorders and diseases of the GI tract such as inflammatory bowel disease [Mantyh et al in Neuroscience (1988) 25 (3) 817–37 and D. Regoli in "Trends in Cluster Headache" Ed. Sicuteri et al, Elsevier Scientific Publishers, Amsterdam (1987) page 85)]. It is also hypothesised that there is a neurogenic mechanism for arthritis in which substance P may play a role [Kidd et al "A Neurogenic Mechanism for Symmetrical Arthritis" in The Lancet, 11 November 1989 and Grünblad et al "Neuropeptides in Synovium of Patients with Rheumatoid Arthritis and Osteoarthritis" in J. Rheumatol (1988) 15(12) 1807–10]. Therefore, substance P is believed to be involved in the inflammatory response in diseases such as rheumatoid arthritis and osteoarthritis [O'Byrne et al in Arthritis and Rheumatism (1990) 33 1023–8]. Other disease areas where tachykinin antagonists are believed to be useful are allergic conditions [Hamelet et al Can. J. Pharmacol. Physiol. (1988) 66 1361-7], immunoregulation [Lotz et al Science (1988) 241 1218-21 and Kimball et al. J. Immunol. (1988) 141 (10) 3564-9]vasodilation, bronchospasm, reflex or neuronal control of the viscera [Mantyh et al, PNAS (1988) 85 3235-9]and, possibly by arresting or slowing β-amyloid-mediated neurodegenerative changes [Yankner et al, Science (1990) 250, 79–82] in senile dementia of the Alzheimer type, Alzheimer's disease and Down's Syndrome.

Substance P may also play a role in demyelinating diseases such as multiple sclerosis and amyotrophic lateral sclerosis [J. Luber-Narod et al, poster to be presented at C.I.N.P. XVIIIth Congress, 28th June-2nd July 1992, in press].

In view of their metabolic instability, peptide derivatives are likely to be of limited utility as therapeutic agents. It is for this reason that non-peptide tachykinin antagonists are sought.

WO-A-90/05729 describes inter alia a class of cis-3-[cyclic]methylamino-2-[(α-substituted)arylmethyl]-quinuclidine compounds which are stated to be useful as substance P antagonists for treating gastrointestinal disorders, central nervous system disorders, inflammatory diseases and pain or migraine. There is, however, no disclosure or suggestion in WO-A-90/05729 of the arylmethyloxy- or arylmethylthiosubstituted azabicyclic derivatives provided by the present invention.

We have now found a further class of non-peptides which are potent antagonists of tachykinin.

The present invention provides a compound of formula (I), or a salt or prodrug thereof:

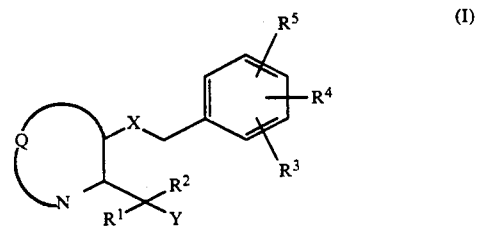

wherein
Q is the residue of an optionally substituted azabicyclic ring system;
X represents oxa or thia;
Y represents H or hydroxy;
$R^1$ and $R^2$ independently represent phenyl or thienyl, either of which groups may be optionally substituted by halo or trifluoromethyl;
$R^3$, $R^4$ and $R^5$ independently represent H, $C_{1-6}$ alkyl, $C_{2-6}$ alkenyl, $C_{2-6}$ alkynyl, halo, cyano, nitro, trifluoromethyl, trimethylsilyl, $-OR^a$, $SCH_3$, $SOCH_3$, $SO_2CH_3$, $-NR^aR^b$, $-NR^aCOR^b$, $-NR^aCO_2R^b$, $-CO_2R^a$ or $-CONR^aR^b$; and
$R^a$ and $R^b$ independently represent H, $C_{1-6}$ alkyl, phenyl or trifluoromethyl.

The azabicyclic ring system of which Q is the residue is a non-aromatic ring system containing, as the sole heteroatom, the nitrogen atom indicated in formula (I) above. Suitably the ring system contains from 6 to 10 ring atoms, preferably from 7 to 9 ring atoms. The azabicyclic ring system may be fused, spiro or bridged, preferably bridged. The azabicyclic ring system may be substituted by one or more groups selected from carbonyl, $C_{1-4}$alkyl, $C_{2-4}$alkenyl, $C_{2-4}$alkynyl, halo, hydroxy, $C_{1-4}$alkoxy, carboxy or $C_{2-4}$alkoxycarbonyl. Examples of such azabicyclic ring systems include:

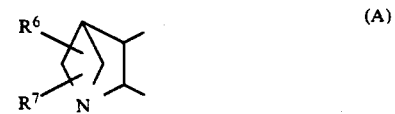

(A)

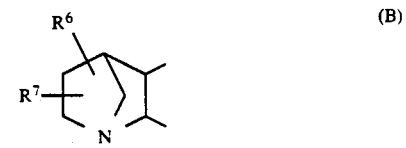

(B)

-continued

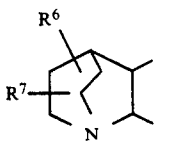
(C)

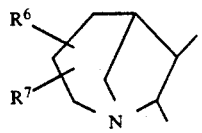
(D)

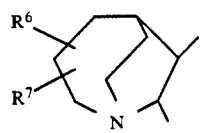
(E)

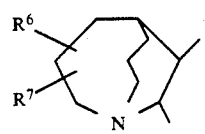
(F)

wherein
$R^6$ and $R^7$ independently represent H, $C_{1-4}$ alkyl, $C_{2-4}$ alkenyl, $C_{2-4}$ alkynyl, halo, hydroxy, $C_{1-4}$ alkoxy, carboxy or $C_{2-4}$ alkoxycarbonyl; or $R^6$ and $R^7$ together represent carbonyl.

It will be appreciated that the nitrogen atom in the azabicyclic ring system will carry a lone pair of electrons.

It will also be appreciated that the $R^6$ and $R^7$ substituents may be present at any position in the azabicyclic ring system, including, where appropriate, the bridgehead carbon atom depicted in structures A to F above.

Suitably the group $R^6$ is H or methyl; and $R^7$ is H, $C_{1-4}$ alkyl, hydroxy or $C_{1-4}$ alkoxy, preferably H, methyl, hydroxy or methoxy. Preferably one or more preferably both of $R^6$ and $R^7$ is/are H.

Suitably the azabicyclic ring system of which Q is the residue is a 1-azabicyclo[2.2.1]heptanyl (1-azanorbornanyl), 1-azabicyclo[2.2.2]octanyl (quinuclidinyl) or 1-azabicyclo[3.2.1]octanyl ring system of formula B, C or D above, respectively, any of which is optionally substituted by methyl or hydroxy. A preferred ring system is quinuclidine of formula C above.

The alkyl, alkenyl and alkynyl groups referred to with respect to any of the formulae herein may represent straight, branched or cyclic groups. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkylalkyl groups such as cyclopropylmethyl; suitable alkenyl groups include vinyl and allyl; and suitable alkynyl groups include propargyl.

The term "halo" as used herein includes fluoro, chloro, bromo and iodo.

Preferably X is oxa.
Preferably Y is H.
Preferably, $R^1$ and $R^2$ are identical. In a particularly preferred embodiment, $R^1$ and $R^2$ each represents unsubstituted phenyl.

When Y is hydroxy, suitably, $R^3$, $R^4$ and $R^5$ independently represent H, $C_{1-6}$ alkyl, $C_{2-6}$ alkenyl, $C_{2-6}$ alkynyl, halo, cyano, nitro, trifluoromethyl, —$OR^a$, —$NR^aR^b$, —$NR^aCOR^b$, —$NR^aCO_2R^b$, —$CO_2R^a$, —$CONR^aR^b$, $SCH_3$ or $SO_2CH_3$.

Suitable values for the groups $R^3$, $R^4$ and $R^5$ when Y is H include H, $C_{1-6}$ alkyl, $C_{2-6}$ alkenyl, $C_{2-6}$ alkynyl, halo, cyano, nitro, trifluoromethyl, —$OR^a$, $SCH_3$, $SOCH_3$, $SO_2CH_3$, —$NR^aR^b$, —$NR^aCOR^b$, —$NR^aCO_2R^b$, —$CO_2R^a$ or —$CONR^aR^b$.

More suitably, $R^3$, $R^4$ and $R^5$ independently represent H, $C_{1-6}$ alkyl, $C_{2-6}$ alkenyl, $C_{2-6}$ alkynyl, halo, cyano, nitro, trifluoromethyl, —$OR^a$, —$NR^aR^b$, —$NR^aCOR^b$, —$NR^aCO_2R^b$, —$CO_2R^a$ or —$CONR^aR^b$; and $R^a$ and $R^b$ independently represent H or $C_{1-6}$ alkyl.

For example, suitable values for the groups $R^3$, $R^4$ and $R^5$ include H, amino, nitro, trifluoromethyl, trimethylsilyl, halo, cyano, methyl, ethyl, cyclopropyl, vinyl, carbonylmethoxy, methoxy and phenoxy, more suitably H, nitro, trifluoromethyl and halo, such as chloro.

Preferably, at least one of $R^3$, $R^4$ and $R^5$ is other than H. More preferably, two of $R^3$, $R^4$ and $R^5$ are other than H. The (non-H) substituents are preferably at the 3- and 5-positions of the phenyl ring. In a particularly preferred group of compounds of formula (I), two of $R^3$, $R^4$ and $R^5$ are trifluoromethyl and the other is H.

In one group of compounds, Q is optionally substituted quinuclidinyl or optionally substituted azabicyclo[2.2.1]heptanyl;

$R^1$ and $R^2$ independently represent phenyl, optionally substituted by halo; $R^3$, $R^4$ and $R^5$ independently represent H, $C_{1-6}$alkyl, $C_{2-6}$alkenyl, halo, cyano, nitro, trifluoromethyl, trimethylsilyl, —$OR^a$, —$NR^aR^b$ or —$CO_2R^a$; and $R^a$ and $R^b$ independently represent H, $C_{1-6}$alkyl or phenyl.

In this group of compounds, suitably Y is H; $R^3$, $R^4$ and $R^5$ independently represent H, $C_{1-6}$alkyl, $C_{2-6}$alkenyl, halo, cyano, nitro, trifluoromethyl, —$OR^a$, $NR^aR^b$ or —$CO_2R^a$; and $R^a$ and $R^b$ independently represent H or $C_{1-6}$alkyl.

The compounds according to the invention have at least two asymmetric centres, and may accordingly exist both as enantiomers and as diastereoisomers. In particular, the relative orientation of the substituents on the azabicylic ring system in formula (I) above may give rise to cis and trans diastereoisomers. It is to be understood that all such isomers and mixtures thereof are encompassed within the scope of the present invention.

It is believed that of the cis diastereomers, tachykinin receptor antagonist activity preferentially resides in the 2S,3S diastereomer, whereas of the trans diastereomers, activity preferentially resides in the 2R,3S diastereomers. Thus, it is believed that S stereochemistry at the 3-position of the azabicyle is crucial to tachykinin receptor antagonist activity.

A particular sub-class of compounds according to the invention is represented by the compounds of formula IIA, and salts and prodrugs thereof:

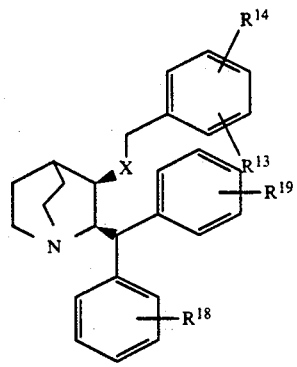

(IIA)

wherein

X represents oxa or thia, preferably oxa;

$R^{13}$ and $R^{14}$ independently represent hydrogen, $C_{1-6}$alkyl, $C_{2-6}$alkenyl, halo, cyano, nitro, —$CO_2(C_{1-6}$alkyl), trifluoromethyl, trimethylsilyl, hydroxy, $C_{1-6}$ alkoxy, phenoxy or amino; and $R^{18}$ and $R^{19}$ independently represent hydrogen, halo or trifluoromethyl.

Particular values of $R^{13}$ and $R^{14}$ include hydrogen, $C_{1-5}$alkyl, especially methyl, ethyl and cyclopropyl, $C_{2-6}$alkenyl, especially vinyl, halo, nitro, trifluoromethyl, trimethylsilyl, cyano, methoxy and phenoxy. In one group of compounds of formula (IIA), $R^{13}$ and $R^{14}$ independently represent hydrogen, $C_{1-6}$ alkyl, halo, cyano, nitro, trifluoromethyl, hydroxy, $C_{1-6}$ alkoxy or amino, they may also independently represent phenoxy; for example, hydrogen, $C_{1-5}$ alkyl, especially methyl, halo, especially chloro and fluoro, nitro, trifluoromethyl, cyano, methyl and methoxy. Preferably, $R^{13}$ and $R^{14}$ are selected from hydrogen, nitro, trifluoromethyl and halo, especially chloro. Preferably, at least one of $R^{13}$ and $R^{14}$ is other than hydrogen. More preferably, $R^{13}$ and $R^{14}$ are both other than hydrogen and are located at the 3- and 5-positions of the phenyl ring.

Preferably, $R^{18}$ and $R^{19}$ both represent hydrogen.

A preferred compound of formula (IIA) is cis-(2S,3S)-3-[3,5-bis(trifluoromethyl)benzyloxy]-2-(diphenylmethyl)-1-azabicyclo[2.2.2]octane.

A further sub-class of compounds according to the invention is represented by the compounds of formula (IIB), and salts and prodrugs thereof:

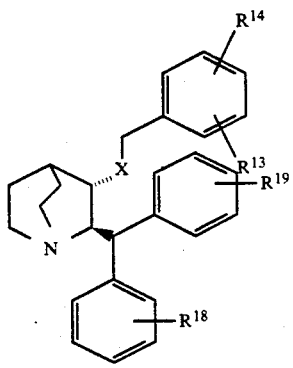

(IIB)

wherein X, $R^{13}$, $R^{14}$, $R^{18}$ and $R^{19}$ are as defined for formula (IIA) above.

Suitably, in formula (IIB) X represents oxa or thia, preferably oxa;

$R^{13}$ and $R^{14}$ independently represent phenoxy or, preferably, hydrogen, $C_{1-6}$ alkyl, halo, cyano, nitro, trifluoromethyl, hydroxy, $C_{1-6}$ alkoxy or amino; and $R^{18}$ and $R^{19}$ independently represent hydrogen, halo or trifluoromethyl.

A preferred group of compounds according to the invention are compounds of formula (IIB) wherein X is oxa and each of $R^{13}$ and $R^{14}$ represents a methyl or a trifluoromethyl group.

Also preferred are compounds of formula (IIB) where X is oxa and each of $R^{13}$ and $R^{14}$ is halo, especially chloro.

A further sub-class of compounds according to the invention is represented by the compounds of formula (IIC), and salts and prodrugs thereof:

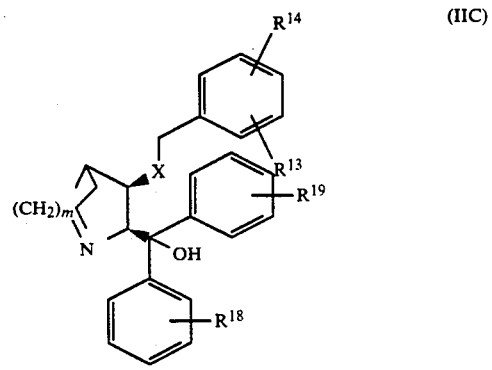

(IIC)

wherein

X represents oxa or thia, preferably oxa;

$R^{13}$ and $R^{14}$ independently represent hydrogen, $C_{1-6}$ alkyl, halo, cyano, nitro, trifluoromethyl, hydroxy, $C_{1-6}$ alkoxy, phenoxy, $OCF_3$, amino, $SCH_3$, $SO_2CH_3$ or $COO(C_{1-6}$ alkyl);

$R^{18}$ and $R^{19}$ independently represent hydrogen, halo or trifluoromethyl; and m is 1 or 2.

Suitably, X, $R^{13}$ $R^{14}$, $R^{18}$ and $R^{19}$ are as defined for formula (IIA) above and m is 1 or 2.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, oxalic acid, fumaric acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The invention also provides pharmaceutical compositions comprising one or more compounds of this invention in association with a pharmaceutically acceptable carrier. Preferably these compositions are in unit dosage form such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The compounds of the present invention are of value in the treatment of a wide variety of clinical conditions which are characterised by the presence of an excess of tachykinin, in particular substance P, activity. These may include disorders of the central nervous system such as anxiety, psychosis and schizophrenia; neurodegenerative disorders such as senile dementia of the Alzheimer type, Alzheimer's disease and Down's syndrome; demyelinating diseases such as MS and ALS; respiratory diseases such as bronchopneumonia, bronchospasm and asthma; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine. Thus, the present invention further provides a compound for use in the manufacture of a medicament for the treatment of physiological disorders associated with an excess of tachykinins, especially substance P. The present invention also provides a method for the the treatment or prevention of physiological disorders associated with an excess of tachykinins, especially substance P, which method comprises administration to a patient in need thereof of a tachykinin reducing amount of a compound or composition of this invention.

In the treatment of conditions involving actions of tachykinins released physiologically in response to noxious or other stimuli, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises reacting a compound of formula (III) with a compound of formula (IV):

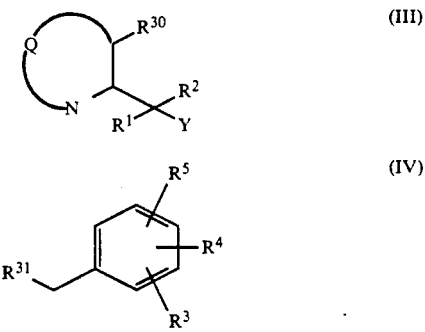

wherein Q, Y, $R^1$, $R^2$, $R^3$, $R^4$ and $R^5$ are as defined for formula (I) above, and one of $R^{30}$ and $R^{31}$ represents a leaving group and the other of $R^{30}$ and $R^{31}$ represents XH, where X is as defined for formula (I); in the presence of a base.

Suitably, when Y is H, $R^{31}$ represents a leaving group and $R^{30}$ represents XH.

Suitable leaving groups include halo, e.g. chloro, bromo or iodo, or sulphonate derivatives such as tosylate or mesylate.

The reaction is conveniently carried out in a suitable organic solvent, such as an ether, e.g. 1,2-dimethoxyethane, at a temperature in the range of −5° to 25° C., preferably about 0° C. Favoured bases of use in the reaction include alkali metal amides and hydrides, such as potassium bis(trimethylsilyl)amide and potassium hydride. Suitably, potassium bis(trimethylsilyl)amide is used.

The intermediates of formula (III) above wherein $R^{30}$ is SH may be prepared from the corresponding intermediates of formula (III) wherein $R^{30}$ represents OH by treating the latter compound with Lawesson's reagent or phosphorus pentasulphide in a suitable solvent, e.g. pyridine, at ambient or elevated temperatures, suitably at reflux temperature.

The intermediates of formula (III) above wherein $R^{30}$ is OH and Y is hydrogen may be prepared by the procedures described in *J. Med. Chem.*, 1974, 17, 497, and *J. Med. Chem.*, 1975, 18. 587; or by methods analogous thereto.

The intermediates of formula (III) above Wherein $R^{30}$ is OH and Y is hydroxy may be prepared by treatment of a compound of formula (V) with a compound of formula (VI):

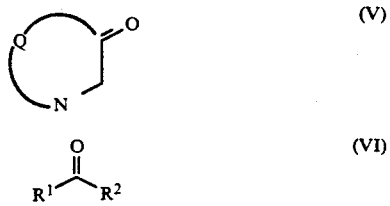

(V)

(VI)

wherein Q, $R^1$ and $R^2$ are as defined for formula (I) above, in the presence of a base.

The reaction is conveniently carried out in an inert organic solvent, such as an ether, e.g. tetrahydrofuran, at low temperature, for example about $-80°$ to about $-40°$ C., preferably about $-78°$ C. Suitable bases will be readily identified by a person skilled in the art and include alkali metal hydrides and amides. A favoured base is lithium bis(trimethylsilyl)amide.

Intermediates of formula (III) wherein $R^{30}$ is OH having cis stereochemistry may preferably be prepared from the corresponding ketones via a selective reduction using a suitable reducing agent such as a lithium aluminium hydride or a substituted borohydride such as triethylborohydride, as described in the accompanying examples.

Intermediates of formula (III) wherein $R^{30}$ is OH having trans sterochemistry may be obtained selectively via a procedure involving non-selective reduction of the corresponding ketone, for example using sodium in an aromatic hydrocarbon solvent, e.g. toluene, preferably in the presence of an alcohol, e.g. iso-propyl alcohol, to give a mixture of cis and trans isomers, followed by selective oxidation of the cis isomer using a ketone in the presence of a base (Oppenauer oxidation). Suitable ketones include acetone, methyl ethyl ketone, cyclohexanone and, preferably, benzophenone. Suitable bases include alkali metal hydrides, e.g. potassium hydride.

Intermediates of formula (III) wherein $R^{30}$ is a leaving group may be prepared from compounds of formula III wherein $R^{30}$ is OH, for example, by reaction with a thionyl halide, a mesyl halide or a tosyl halide.

Where they are not commercially available, the intermediates of formulae (IV), (V) and (VI) above may be prepared by the procedures described in the accompanying examples or by alternative procedures which will be readily apparent to one skilled in the art.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. For example, intermediate alcohols of formula (III), wherein X is oxa, may be resolved into their component enantiomers by standard techniques, such as the formation of diastereomeric esters or amides, followed by chromatographic separation and removal of the chiral auxiliary. The diastereomeric alcohols can then be used to prepare optically pure compounds of formula (I).

During any of the above synthetic sequences it may be necessary and/or desirable to protect sensitive or reactive groups on any of the molecules concerned. This may be achieved by means of conventional protecting groups, such as those described in *Protective Groups in Organic Chemistry*. ed. J. F. W. McOmie, Plenum Press, 1973; and T. W. Greene, *Protective Groups in Organic Synthesis*, John Wiley & Sons, 1981. The protecting groups may be removed at a convenient subsequent stage using methods known from the art.

The following Examples illustrate the preparation of compounds according to the invention.

The compounds of accompanying Examples 1, 2, 4, 7 and 8 were tested at a concentration of 1.0 $\mu$M for their ability to antagonise the contraction elicited by 0.1$\mu$M SPOMe (substance P methyl ester) on the longitudinal muscle of guinea pig ileum (isometric contraction) and caused an inhibition of greater than 70% in each case.

DESCRIPTION 1

($\pm$)-cis-2-(Diphenylmethyl)-1-azabicyclo[2.2.2]octan-3-ol 2-(Diphenylmethyl)-1-azabicyclo[2.2.2]octan-3-one (50 g) was dissolved in dimethoxyethane (400 ml) and the solution stirred under nitrogen. Lithium triethylborohydride (1.0M in THF, 200 ml) was added dropwise to the stirred solution over a period of 1 h. The excess reducing agent was destroyed by dropwise addition of hydrochloric acid (1N). The solvent was removed in vacuo, the residue was made basic with sodium hydroxide (2N) and extracted with dichloromethane (4$\times$500 ml). The organic extract was dried (MgSO$_4$) and evaporated and the residue was recrystalized from toluene: m.p. 192°–194° C., $^1$H NMR (360 MHz, CDCl$_3$) $\delta$1.25–1.4 (1H, m, CH), 1.42 (1H, d, J=5.0Hz, OH), 1.48–1.76 (2H, m, CH$_2$), 1.90–2.04 (2H, m, CH$\times$2), 2.64–2.9 (3H, m, CHN+CH$_2$N), 3.16–3.34 (1H, m, CHN), 3.68 (1H, dd, J=14.5, 18.0Hz, CNH), 4.00 (1H, mc, CHOH), 4.54 (1H, d, J=18.0Hz, Ph$_2$CH), 7.12 (10H, m, ArH).

DESCRIPTION 2

(+) and (−) cis-2-(Diphenylmethyl)-1-azabicyclo[2.2.2octan-3-ol (a)

cis-2-(Diphenylmethyl)-1-azabicyclo[2.2.2]octan-3-yl camphanate: diastereoisomers 1 and 2

A solution of cis-2-(diphenylmethyl)-1-azabicyclo[2.2.2]octan-3-ol (Description 1) (20 g) in dichloromethane (400 ml) was cooled in ice under N$_2$. Dimethylaminopyridine (8.3 g) and triethylamine (6.9 ml) were added to the solution. A solution of (−)-camphanic acid chloride was added dropwise to the solution and the mixture was stirred at room temperature for 45 minutes. It was then washed with aqueous sodium bicarbonate, water and brine. The organic phase was dried (MgSO$_4$) and concentrated in vacuo.

The residue was purified by flash chromatography on silica using 2–4% methanol in dichloromethane as eluant; this yielded the product as a 1:1 mixture of diastereoisomers. This mixture was recrystallized from ethyl acetate; the first crop was isolated and recrystallised twice from ethyl acetate to yield diastereoisomer 2(99.5% pure, HPLC). The mother liquors from the first crystallisation were evaporated and recrystallised from ethyl acetate to give diastereoisomer 1 (99.5% pure, HPLC).

Diastereoisomer 1: mp 231°–232° C.; $\delta_H$ (360 MHz, CDCl$_3$) 0.88 (3H, s, CH$_3$), 0.90 (3H, s, CH$_3$), 1.08 (3H, s, CH$_3$), 1.24–1.36 (1H, m, CH), 1.5–2.0 (8H, m, CH+CH$_2$), 2.6–2.8 (3H, m, CHHN+CH$_2$), 3.2 (1H, mc, CHHN), 3.82 (1H, dd, J=14.5, 18.0 Hz), 4.48 (1H, d, J=18.0Hz, CHPh$_2$), 5.29 (1H, mc, CHOCOR), 7.0–8.38 (10H, m, ArH). [$\alpha$]$_D$ (CDCl$_3$, c=1)= +7.1°.

Diastereoisomer 2: m.p. 250°–251° C.; $\delta$H (360 MHz, CDCl$_3$), 0.61 (3H, s, CH$_3$), 1.0 (3H, s, C(CH$_3$)CH$_3$), 1.06 (3H, s, C(CH$_3$)CH$_3$), 1.35 (1H, m, CH), 1.6–1.7 (5H, m, CH, CH$_2$), 1.67–1.74 (2H, m, CH$_2$CH$_2$N), 2.02 (1H, m, CH), 2.24 (1H, m, quinuclidine bridgehead), 2.7 (3H, m, CHHN+CH$_2$N), 3.14–3.24 (1H, m, CHHN), 4.46 (1H, d, J=12.2Hz, CHPh$_2$), 5.3 (1H, m, —CHOCOR), 7.03–7.3 (10H, m, ArH). [$\alpha$]$_D$ (CDCl$_3$, c=1)= +1.2°.

(b) (+) and (−) cis-2-(Diphenylmethyl)-1-azabicyclo[2.2.2octan-3ol

The camphanate ester (diastereoisomer 1) (0.25 g) was dissolved in dimethoxyethane (10 ml) and stirred under N$_2$. Lithium aluminum hydride (1.0M in diethylether) 0.58 ml was added to the solution dropwise. The mixture was allowed to stir for 2h. Excess lithium aluminium hydride was destroyed by addition of water dropwise followed by sodium hydroxide and water to afford a granular precipitate. MgSO$_4$ was added to the mixture which was filtered through celite to remove inorganic matter. The solvent was evaporated and the residue was recrystallised from isopropanol to afford the alcohol (1) (99.5% enantiomer 1, HPLC): m.p. 174°–175° C.; $\delta_H$ (360 MHz, CDCl$_3$), 1.20–1.30 (1H, m, CH), 1.34 (1H, d, J=4Hz, OH), 1.46–1.7 (2H m, CH$_2$), 1.86–2.0 (2H, m, CH+CH), 2.56–2.90 (3H, m, CHHN+CH$_2$N), 3.10–3.20 (1H, m, CHHN), 3.64 (1H, dd, J=14.5, 18.0Hz, CHCHPh$_2$), 3.96 (1H, m, ChHOH), 4.48 (1H, d, J=18.0Hz, Ph$_2$CH), 7.06–7.46 (10H, m, ArH). C$_{20}$H$_{23}$NO.0.25H$_2$O requires: C, 80.63; H, 7.59; N, 4.70. Found: C, 80.89; H, 7.87; N, 4.73%; [$\alpha$]$_D$ (CDCl$_3$, c=1)= −11.2°.

In a similar procedure camphanate ester (diastereoisomer 2) afforded the alcohol (enantiomer 2, 99.5% optically pure, HPLC): m.p. 172°–173° C.; [$\alpha$]$_D$(CDCl$_3$, c=1)= +11.6°.

DESCRIPTION 3

2-(Diphenylmethyl)-1-azabicyclo[2.2.2]octan-3-ol (mixture of cis/trans 80:20)

2-(Diphenylmethyl)-1-azabicyclo[2.2.2]octan-3-one (18.9 g) was dissolved in tetrahydrofuran (350 ml), anhydrous) and cooled to −65° C. under nitrogen. Lithium aluminium hydride (1.0 M solution in THF, 40 ml) was added dropwise to the solution which was stirred at room temperature overnight. Water (2 ml) followed by sodium hydroxide (15% 2 ml) and water (6 ml) were added dropwise to the solution resulting in precipitation of the inorganic salts. Magnesium sulfate (2 g) was added and the mixture filtered through celite. The solvent was removed in vacuo and the residue was recrystallised from isopropanol affording the pure cis isomer. The mother liquors were concentrated and found to be 80:20 cis/trans by $^1$H NMR; this was used in the examples without further purification.

DESCRIPTION 4 trans-2-(Diphenylmethyl)-1-azabicyclo[2.2.2]-octan-3-ol 2-(Diphenylmethyl)-1-azabicyclo[2.2.2]-octan-3-one (50 g) was dissolved in toluene (650 ml) and warmed to reflux. Sodium (19.2 g) was added portionwise, followed by isopropyl alcohol (160 ml). After 1 hours the mixture was cooled to ambient temperature and then quenched with methanol. Evaporation yielded a brown solid which was partitioned between water and dichloromethane. The organics were dried (MgSO$_4$) and evaporated to give a light brown solid (~50 g), which was suspended in toluene (750 ml) and then heated to reflux with benzophenone (130 g) and sodium hydride (18.9 g, 50% in oil). After 1 hour the mixture was quenched with 2N hydrochloride acid and washed with diethylether. The aqueous layer was basified with sodium hydroxide and the desired product extracted into dichloromethane. After evaporation, the residue was passed through a column of Grade III alumina eluted with 70:30 dichloromethane:petrol to yield the title compound and the starting ketone; m.p. 214°–216° C., $\delta_H$ (360MHz, CDCl$_3$) 1.25–1.90 (5H, 3×m, 2×Ce,uns/H/ 2$\beta$ to N and CH at bridgehead), 2.53–2.60 and 2.8–3.04 (4H, 2×m, 2×CH$_2$ $\alpha$ to N), 3.35 (h, m, CHN), 3.54 (H, broad s, CHOH), 3.94 (H, d, J=12.0Hz, CHPh$_2$), 7.1–7.4 (10H, m, ArH).

DESCRIPTION 5

(+) and (−)-trans-2-(Diphenylmethyl)-1-azabicyclo[2.2.2]-octan-3-ol a) trans-2-(Diphenylmethyl)-1-azabicyclo[2.2.2]-octan-3-yl camphanate:diastereomers A and B A solution of trans-2-(diphenylmethyl)-1-azabicyclo[2.2.2]-octan-3-ol (11.3 g) in dichloromethane (150 ml) and triethylamine (4 ml) was cooled in an ice bath under N$_2$. After dropwise addition of (−)-camphanic acid chloride (10.1 g) in dichloromethane (50 ml), the mixture was stirred at room temperature for 45 minutes. It was then washed with aqueous sodium bicarbonate (150 ml) followed by brine (150 ml), dried (Na$_2$SO$_4$) and evaporated. The residue was passed through a column of Grade III alumina eluted with 2.5% methanol in dichloromethane to yield the desired product (1:1 mixture of diastereoisomers).

the title compound (18 g, 1:1 mixture of diastereoisomers) was recrystallised from methanol/dichloromethane. The first crop was removed and recrystallised twice again from the same solvents to yield diastereoisomers B. The mother liquors from the first crystallisation were evaporated and recrystallised from ethyl acetate/petrol to give diastereoisomer A.

Diastereoisomer A: m.p. 206°–208° C. $\delta_H$ (250 MHz, CDCl$_3$) 0.80 (3H, s, CH$_3$), 0.89 (3H, s, CH$_3$), 107 (3H, s, CH$_3$), 1.32–2.13 (9H, m, 2×CH$_2$ on camphanate bicycle, 2×CH$_2$ $\beta$ to N on quinuclidine, CH at bridgehead), 2.52–2.64 (H, m) and 2.87–3.05 (3H, m, 2×CH$_2$ $\alpha$ to N), 3.68 (H, dd, J=12.0Hz, 4.0Hz, CH $\alpha$ to N), 3.97 (H, d, J=12.0Hz, CHPh$_2$), 4.78–4.80 (H, m CHO); 7.06–7.34 (10H, m, ArH); [$\alpha$]$_D$ (CDCl$_3$, c=1)= −58.8°.

Diastereoisomer B: m.p. >250° C. $\delta_H$ (250MHz, CDCl$_3$) 0.75 (3H, s, CH$_3$), 0.95 (3H, s, CH$_3$); 1.07 (3H, s, CH$_3$), 1.39-2.12 (9H, m, 2×CH$_2$ on camphanate bicycle, 2×CH$_2\beta$ to N on quinuclidine, CH at bridgehead), 2.49-2.82 (H, m) and 2.86-3.03 (3H, m, 2×CH$_2\delta$ N), 3.55-3.62 (h, dd, J=12.0Hz, 4.0Hz, CH$\alpha$ to N), 3.95-3.99 (H, d, J=12.1Hz, CHPh$_2$), 4.82-4.85 (H, m, CHO), 7.07-7.34 (10H, m, ArH). [$\alpha$]$_D$ (CDCl$_3$, c=1)= +42.2°.

(b) (+) and (−)trans-2-(Diphenylmethyl)-1-azabicyclo[2.2.2]-octan-3-ol

Diastereoisomer A (3g, >99.5% by HPLC) was taken up in ethanol (120 ml). A solution of potassium hydroxide (0.6 g) in ethanol (30 ml) was added and the mixture heated to reflux for 7 hours. Evaporation of the solvent yielded a white residue which was partitioned between 2N HCl and dichloromethane. The aqueous layer was separated, basified (KOH) and extracted into dichoromethane. This organic extract was washed with brine, dried (Na$_2$SO$_4$) and evaporated to give a white solid which was recrystallised from IPA to afford the title compound, Enantiomer A; m.p. 214°-216° C. $\delta_H$ (360MHz, CDCl$_3$) 1.34-1.66 (3H, m) and 1.90 (H, m, 2×CH$_2\beta$ to N); 1.60 (H, m, CH at bridgehead); 2.59 (H, m): 2.85 (2H, m) and 3.02 (H, m, 2×CH$_2\alpha$to N); 3.36-3.42 (H, m, CHN); 3.56 (H, broad s, CHO); 3.93-3.97 (H, d, J=11.9Hz, CHPh$_2$); 7.13-7.39 (10H, m, ArH). [$\alpha$]$_D$ (methanol, c=1) = −152.4°.

Similarly, diastereoisomer B was hydrolysed as above to afford the alcohol, enantiometer B: [$\alpha$]$_D$(methanol, c=1)= +151.5°.

EXAMPLE 1 cis-2-(Diphenylmethyl)-3-(3-nitrobenzyloxy)-1-azabicyclo[ 2.2.2]octane oxalate cis-2-(Diphenylmethyl)-1-azabicyclo[2.2.2]octan-3-ol (Description 2) (0.46 g) was dissolved in dimethoxyethane (15 ml, anhydrous) with heating. The solution was cooled to 0° C. (ice-methanol) and 18-crown-6 (10 mg) was added. Potassium bis(trimethylsilyl)amide (0.5M in toluene, 3.6 ml) was added dropwise. The solution was stirred at 0° C. for 15 min. A solution of 3-nitrobenzyl bromide (0.39 g) in dimethoxyethane (5 ml) was added in one portion. The mixture was stirred for 1 hour and was quenched with water. The solvent was evaporated in vacuo and the residue was diluted with water and dichloromethane. The organic layer was washed with saturated sodium chloride, dried (magnesium sulfate) and evaporated in vacuo. The residue was purified by chromatography on alumina using ether-hexane (20:80) as the eluant and gradient elution to 50% ether. This furnished the product as a white crystalline solid (320 mg, 50%). Treatment of an ethereal solution of the free base with ethereal oxalic acid precipitated the oxalate salt; this was recrystallised from isopropanol, m.p. 224°-226° C. (from IPA).

Found: C, 66.94; H, 5.97; N, 5.34. C$_{27}$H$_{28}$N$_2$O$_3$. C$_2$O$_2$H$_2$ requires: C, 67.17; H, 5.83; N, 5.40%.

The compounds of Examples 2 to 30 were prepared according to the method described in Example 1.

EXAMPLE 2 cis-2-(Diphenylmethyl)-3-[2-(trifluoromethyl)benzyloxy]-1-azabicyclo[2.2.2]octane oxalate cis-2-(Diphenylmethyl)-1-azabicyclo[2.2.2]octan-3-ol (0.52 g) and 2-trifluoromethyl)benzyl bromide (0.33 ml) gave the title compound; m.p. 247°-248° C. (from IPA).

Found: c, 66.44; H, 5.74; N, 2.71. Calcd. for C$_{28}$H$_{28}$F$_3$NO. C$_2$O$_4$H$_2$: C, 66.53; H, 5.58; N, 2.59%.

EXAMPLE 3 cis-3-(2-Chlorobenzyloxy)-2-(diphenylmethyl)-1-azabicyclo[2.2.2]octane oxalate cis-2-(Diphenylmethyl)-1-azabicyclo[2.2.2]octan-3-ol (0.54 g) and 2-chlorobenzyl chloride (0.34 g) gave the title compound, m.p. 221°-223° C. (from IPA).

Found: C, 68.43; H, 5.91; N, 2.63; Cl, 7.17. C$_{27}$H$_{28}$ClNO. C$_2$O$_4$H$_2$ requires: C, 68.56; H, 5.95; N, 2.76; Cl, 6.98%.

EXAMPLE 4 cis-3-(3-Chlorobenzyloxy)-2-(diphenylmethyl)-1-azabicyclo[2.2.2]octane oxalate cis-2-(Diphenylmethyl)-1-azabicyclo[2.2.2]octan-3-ol (0.5 g) and 3-chlorobenzyl bromide (0.4 g) gave the title compound, m.p. 221° C. (from IPA).

Found C, 63.61; H, 5.94; N, 2.72. C$_{27}$H$_{29}$ClNO. C$_2$O$_2$ requires C, 68.49; H, 6.13; N, 2.75%.

EXAMPLE 5 cis-3-8 3.5-Bis(trifluoromethyl)benzyloxy]-2-(diphenylmethyl)-1-azabicyclo[2.2.2]octane oxalate cis-2-(Diphenylmethyl)-1-azabicyclo[2.2.2]octan-3-ol (0.5 g) and bis(trifluoromethyl)benzyl bromide (0.4 g) gave the title compound, m.p. 224° C. (from IPA).

Found: C, 60.52; H, 4.97; N, 2.30; C$_{28}$H$_{29}$F$_6$NO. C$_2$O$_4$H$_2$ requires C, 60.98; H, 4.95; N, 2.29%.

EXAMPLE 6 cis-2-(Diphenylmethyl)-3-[4-(trifluoromethyl)benzyloxy]-1-azabicyclo[2.2.2]octane oxalate cis-2-(Diphenylmethyl)-1-azabicyclo[2.2.2]octan-3-ol (0.5 g) and 4-trifluoromethyl)benzyl bromide (0.4 g) gave the title compound, m.p. 195° C. (from IPA)

Found: C, 66.40; H, 5.71; N, 2.62; C$_{28}$H$_{28}$F$_3$NO. C$_2$O$_4$H$_2$ requires C, 66.41; H, 5.75; N, 2.58%.

EXAMPLE 7 cis-3-(3,5-Difluorobenzyloxy)-2-(diphenylmethyl)-1-azabicyclo[2.2.2]octane oxalate m.p. 212° C.

C$_{27}$H$_{27}$F$_2$NO (CO$_2$H)$_2$ requires: C, 68.22; H, 5.92; N, 2.74. Found: C, 68.39; H, 5.86; N, 2.75%.

EXAMPLE 8 cis-2-(Diphenylmethyl)-3-(4-methoxybenzyloxy)-1-azabicyclo[2.2.2]octane oxalate m.p. 205°-207° C.

C$_{28}$H$_{31}$NO$_2$ (CO$_2$H)$_2$ requires: C, 71.57; H, 6.56; N, 2.78. Found: C, 71.43; h, 6.86; N, 2.85%.

EXAMPLE 9 cis-2-(Diphenylmethyl)-3-(3-methoxybenzyloxy)-1-azabicyclo[2.2.2]octane oxalate m.p. 207°-209° C.

C$_{28}$H$_{31}$NO$_2$ (CO$_2$H)$_2$ requires: C, 71.57; H, 6.56; N, 2.78. Found: C, 71.19; H, 6.73; N, 2.70%.

EXAMPLE 10 cis-3-(2-Cyanobenzyloxy)-2-(diphenylmethyl)-1-azabicyclo[2.2.2]octane oxalate.

m.p. 231°–233° C.

$C_{28}H_{28}N_2O.(CO_2H)_{1.1}$ requires: C, 71.46; H, 6.00; N, 5.52. Found: C, 71.62; H, 6.01; N, 5.31%.

EXAMPLE 11 cis-3-(3-Cyanobenzyloxy)-2-(diphenylmethyl)-1-azabicyclo[2.2.2]octane oxalane.

m.p. 229√–231° C.

$C_{28}H_{28}N_2O.C_2H_2O_4$ requires: C, 72.27; H, 6.06; N, 5.62. Found: C, 71.88; H, 6.20; N, 5.43%.

EXAMPLE 12 cis-2-(Diphenylmethyl)-2-(3-trifluoromethylbenzyloxy)-1-azabicyclo[2.2.2]octane oxalate m.p. 209°–210° C.

$C_{28}H_{28}F_3NO (COOH)_2$ requires: C, 66.53; H, 5.58; N, 2.59. Found: C, 66.16; H, 5.60; N, 2.71%.

EXAMPLE 13 cis-3-(3,5-Dimethylbenzyloxy)-2-(diphenylmethyl)-1-azabicyclo[2.2.2]octane oxalate m.p. 234°–236° C.

$C_{29}H_{33}NO.(COOH)_2.0.25H_2O$ requires: C, 73.57; H, 7.07; N, 2.77. Found: C, 73.23; H, 6.63; N, 2.89%.

EXAMPLE 14 cis-3-(2,5-Difluorobenzyloxy)-2-diphenylmethyl-1-azabicyclo[2.2.2]octane oxalate.

m.p. 205°–207° C.

$C_{27}H_{27}F_2NO(COOH)_2.0.25H_2O$ requires: C, 67.76; H, 5.78; N, 2.72. Found: C, 67.92; H, 5.68; N, 2.66%.

EXAMPLE 15 cis-2-(Diphenylmethyl)-3-(3-fluorobenzyloxy)-1-azabicyclo[2.2.2]octane oxalate.

m.p. 213°–215° 1 C.

$C_{27}H_{28}FNO (COOH)_2.0.25H_2O$: requires: C, 70.22; H, 6.19; N, 2.83. Found: C, 70.30; H, 5.98; N, 2.78%.

EXAMPLE 16 cis-2-(Diphenylmethyl)-3-(2-fluorobenzyloxy)-1-azabicyclo[2.2.2.]octane oxalate.

m.p. 200°–202° C.

$C_{27}H_{28}FNO (COOH)_2.0.5H_2O$: requires: C, 69.59; H, 6.24; N, 2.80. Found: C, 69.97; H, 6.07; N, 2.72%.

EXAMPLE 17 cis-3-(2,5-Dimethylbenzyloxy)-2-(diphenylmethyl)-1-azabicyclo[2.2.2]octane oxalate.

m.p. 227°–229° C.

$C_{29}H_{33}NO (COOH)_2.0.5H_2O$: requires: C, 72.92; H, 7.10; N, 2.74. Found: C, 72.59; H, 6.78; N, 2.63%.

EXAMPLE 18 cis-2-(Diphenylmethyl)-3-(3-methylbenzyloxy)-1-azabicyclo[2.2.2]octane oxalate.

m.p. 199°–201° C.

$C_{28}H_{31}NO (COOH)_2.0.25H_2O$: requires: C, 73.22; H, 6.80; N, 2.85. Found: C, 73.20; H, 6.77; N, 2.79%.

EXAMPLE 19 cis-3-(4-Chlorobenzyloxy)-2-(diphenylmethyl)-1-azabicyclo[2.2.2]octane oxalate.

m.p. 183°–185° C.

$C_{27}H_{28}ClNO.1.3 (COOH)_2$: requires: C, 66.45; H, 5.77; N, 2.62. Found: C, 66.78; H, 5.38; N, 2.66%.

EXAMPLE 20 cis-3-(Benzyloxy)-2-(diphenylmethyl)-1-azabicyclo[2.2.2]octane oxalate.

m.p. 198°–199° C.

$C_{27}H_{29}NO. (C_2O_4H_2)1.5$ requires C, 69.62; H, 6.03; N, 2.71. Found: C, 69.51; H, 6.33; N, 2.61%.

EXAMPLE 21 cis-2-(Diphenylmethyl)-3-(4-methylbenzyloxy)-1-azabicyclo[2.2.2]octane oxalate.

m.p. 196°–198° C.

$C_{28}H_{31}NO. (CO_2H)_20.5 (H_2O)$ requires: C, 73.22; H, 6.86; N, 2.85. Found: C, 73.45; H, 6.82; N, 2.85%.

EXAMPLE 22 cis-3-(3,4-Dimethylbenzyloxy)-2-(diphenylmethyl)-1-azabicyclo[2.2.2]octane oxalate.

m.p. 202°–204° C.

$C_{29}H_{33}NO (CO_2H)_2$ requires C, 74.23; H, 7.03; N, 2.79. Found: C, 74.40; H, 6.90; H, 2.81%.

EXAMPLE 23 cis-2-(Diphenylmethyl)-3-(4-fluorobenzyloxy)-1-azabicylo[2.2.2]octane oxalate.

m.p. 196°–198° C.

$C_{27}H_{28}FNO (CO_2H)_20.75 (H_2O)$ requires: C, 68.96; H, 6.27; N, 2.77. Found: C, 69.06; H, 6.06; N, 2.71%.

EXAMPLE 24 cis-2-(Diphenylmethyl)-3-(2-methylbenzyloxy)-1-azabicyclo [2.2.2]octane oxalate.

m.p. 226° C.

$C_{28}H_{31}NO. C_2O_4H_2$ requires: C, 73.89; H, 6.82; N, 2.87. Found: C, 73.01; H, 6.85; N, 2.91%.

EXAMPLE 25 cis-3-(4-Cyanobenzyloxy)-2-(diphenylmethyl)-1-azabicyclo[2.2.2]octane oxalate.

m.p. 234°–236° C.

$C_{28}H_{28}N_2O.(CO_2H)_2.0.25(H_2O)$ requires: C, 71.62; H, 6.11; N, 5.57. Found: C, 71.22; H, 6.10; N, 5.58%.

EXAMPLE 26 cis-3-(2-Bromobenzyloxy)-2-(diphenylmethyl)-1-azabicyclo[2.2.2]octane oxalate.

m.p. 239°–236° C.

$C_{27}H_{28}BrNO. (COOH)_2$ requires: C, 63.05; H, 5.47; N, 2.53. Found: C, 62.67; H, 5.57; N, 2.51%.

EXAMPLE 27 cis-3-(3,5-Dichlorobenzyloxy)-2-(diphenylmethyl)-1-azabicyclo[2.2.2]octane oxalate.

m.p. 243°–244° C. $C_{27}H_{27}Cl_2NO. C_2H_4O_2.0.5H_2O$ requires: C, 63.16; H, 5.48; N, 2.54. Found: C, 63.35; H, 5.32; N, 2.70%.

EXAMPLE 28 cis-3-(3,5-Dimethoxybenzyloxy)-2-(diphenylmethyl)-1-azabicyclo[2.2.2]octane oxalate.

m.p. 195°–197° C.

$C_{29}H_{33}NO_3.1.1$ $(C_2O_4H_2)$ requires: C, 69.06; H, 6.54; N, 2.58. Found: C, 68.87; H, 6.58; N, 2.55%.

EXAMPLE 29 cis-2-(Diphenylmethyl)-3-(3-methoxy,-5-methylbenzyloxy)-1-azabicyclo[2.2.2]octane oxalate.

m.p. 209°–211° C. $C_{29}H_{33}NO_2$ $(CO_2H)_2$. 0.25 ($H_2O$) requires: C, 71.31; H, 6.85; N, 2.68. Found: C, 71.07; H, 6.65; N, 2.78%.

EXAMPLE 30 cis-2-(Diphenylmethyl)-3-(3-phenoxybenzyloxy)-1-azabicyclo[2.2.2]octane oxalate.

m.p. 217°–219° C.

$C_{33}H_{33}NO_2$. $C_2O_4H_2$ requires: C, 74.32; H, 6.24; N, 2.48. Found: C, 74.47; H, 6.29; N, 2.46%.

EXAMPLE 31

(+)-cis-(2S,3S)-3-[3,5-Bis(trifluoromethyl)benzyloxy]-2-(diphenylmethyl)-1-azabicyclo[2.2.2]octane hydrochloride (−) cis-2-(Diphenylmethyl)-1-azabicyclo[2.2.2]octan-3-ol (Description 2, enanatiomer 1) (5.75 g) was suspended in anhydrous dimethoxyethane (100 ml) under $N_2$. Potassium bis(trimethylsilyl)amide (46 ml, 0.5M in toluene) was added dropwise to the stirred mixture to afford a light brown solution. After stirring for 1 hour at room temperature 3,5-bis(trifluoromethyl)-benzyl bromide (6.7 ml) was added and the mixture was stirred for 10 min, affording a deep purple mixture. The solvent was removed in vacuo and the residue was purified by chromatography on alumina (III) using hexane/ether (70:30) as eluent. This removed the unreacted alcohol (2.7 g). The crude fractions containing the ether were purified further by medium pressure chromatography on silica (Lobar) using 3% methanol DCM as eluent. This afforded the ether as a white crystalline solid which was converted to the hydrochloride salt with methanolic hydrogen chloride; recrystallisation from methanol/ethyl acetate afforded the title compound: m.p. >250° C.; $\delta_H$ (360 MHz, $CDCl_3$ free base) 1.26–1.39 (1H, m, CHH), 1.5–1.60 (1H, m, CHH), 1.66–1.88 (2H, m, $CH_2$), 2.16 (1H, mc, CH-bridgehead), 2.70 (1H, mc, CHHN), 2.83 (2H, mc, $CH_2$N), 3.10–3.20 (1H, m, CHHN), 3.56 (1H, d, J=11.5 Hz, OCHHPh), 3.64 (1H, mc, NCHCHO), 3.78 (1H, dd, J=8.0, 11.0 Hz, NCHCHPh$_2$), 4.23 (1H, d, J=11.5 Hz, OCHHPh), 4.45 (1H, d, J=11.0 Hz, CHPh$_2$), 7.08–7.25 (10H, m, ArH), 7.46 (2H, s, ArH), 7.76 (1H, s, ArH). MS (FAB+) 520 (M+ +1, 100%).

$C_{29}H_{27}F_6NO.HCl.0.25H_2O$ requires: C, 62.14; H, 5.13; N, 2.50; Cl, 6.33. Found: C, 62.01; H, 5.13; N, 2.50; Cl, 6.33%. $[\alpha]_D$ (methanol, c=1)= +29.1°.

EXAMPLE 32

(−)-cis-(2R,3R)-3-[3,5-Bis(trifluoromethyl)benzyloxy]-2-(diphenyl-methyl)-1-azabicyclo[2.2.2]octane hydrochloride (+)-cis-2-(Diphenylmethyl)-1-azabicyclo[2.2.2]octan-3-ol (enantiomer 2), Description 2 was reacted according to the procedure described for Example 31 to afford the title compound, m.p. (ethyl acetate-methanol)>250° C.

$C_{29}H_{27}F_6NO.HCl.0.75H_2O$ requires: C, 61.16; H, 5.22; N, 2.46; Cl, 6.23. Found: C, 61.14; H, 5.25; N, 2.49; Cl, 6.78% $[\alpha]_D$ (methanol, c=1)= −27°. MS (FAB+) 520 (M+ +1, 100%).

EXAMPLE 33 cis-2-(Diphenylmethyl)-3-[(3-methyl-5-trimethylsilyl)-benzyloxy]-1-azabicyclo[2.2.2]octane a) 3-Methyl-5-(trimethylsilyl)benzyl bromide

5-Bromo-m-xylene (12 g) was added carefully via a dropping funnel to magnesium turnings (2.33 g) in THF under nitrogen. An iodine crystal was used to initiate the reaction. The mixture was heated at reflux for 2 hrs. When cooled, freshly distilled trimethylsilyl chloride (16.4 ml) was added carefully and the reaction mixture was stirred for 0.5 h. The solvent was removed in vacuo. The residue was washed with ammonium chloride solution, extracted with diethyl ether and dried (magnesium sulphate). The ether was removed in vacuo to afford a light brown oil (10.1 g). This oil (7.1 g) was dissolved in carbon tetrachloride (40 ml) under nitrogen. N-bromosuccinimide (7.1 g) and AIBN (catalytic amount) were added and the mixture was heated to 60° C. for 2 hrs. The solvent was removed in vacuo and the residue purified by chromatography on silica using hexane as eluent. This isolated the desired product as a brown oil.

$\delta_H$ (360 MHz, $CDCl_3$) 0.26 (9H, s, Si($CH_3$)$_3$, 2.35 (3H, s, $CH_3$), 4.47 (2H, s, $CH_2$Br), 7.20 (1H, s, Ar—H), 7.24 (1H, s, Ar—H), 7.30 (1H, s, Ar—H).

b) cis-2-(Diphenylmethyl)-3-[(3-methyl-5-trimethyl silyl)benzyloxy]-1-azabicyclo[2.2.2]octane The compound of Description 1 (2 g) was suspended in anhydrous dimethoxyethane (20 ml) under nitrogen. Potassium bis(trimethylsilyl)amide (16.4 ml, 0.5M in toluene) was added dropwise to the stirred mixture to afford a light brown solution. After stirring for 1 hour at room temperature 3-methyl-5-(trimethylsily(benzyl bromide (2.1 g) and a catalytic amount of 18-Crown-6 were added and the mixture allowed to stir overnight. The solvent was removed in vacuo. The residue was suspended in water and extracted with dichloromethane. The combined organic fractions were washed with brine, dried (magnesium sulphate) and concentrated in vacuo. The residue was purified by chromatography on alumina (III) using hexane/ether (70:30) as eluent. The crude fractions containing the ether were purified further by medium pressure chromatography on silica (Lobar) using 5% MeOH in DCM as eluent. This afforded the ether as a white solid. Recrystallisation of the free base from hexane/DCM afforded the title compound: m.p. 114°–116° C.

$\delta_H$ (360 MHz, $CDCl_3$) 0.26 (9H, s, Si($CH_3$)$_3$), 1.22–1.34 (1H, m, NCH$_2$CHH), 1.42–1.74 (2H, m, NCH$_2$CHH+NCH$_2$CHH), 1.82–1.94 (1H, m, NCH$_2$CHH), 2.08–2.16 (1H, m, NCH$_2$CH$_2$CH), 2.32 (3H, s, CH$_3$), 2.6–2.71 (1H, m, NCHH), 2.76–2.88 (2H, m, NCHH+NCHH), 3.08–3.20 (1H, s, NCHH), 3.50–3.62 (2H, m+d, J=10.5 Hz, CHO+OCHH), 3.68–3.77 (1H, m, NCHCHPh$_2$), 4.01–4.04 (1H, d, J=10.5 Hz, OCHH), 4.30–4.53 (1H, d, J=11 Hz, CHPh$_2$), 6.73 (1H, s, ArH), 7.04–7.38 (12H, m, Ar—H). MS (ACE) 470 (M+ +1, 100%). $C_{31}H_{39}NOSi$ requires:

C, 79.26; H, 8.37, N, 2.98; Found: C, 79.01; H, 8.25; N, 3.03.

EXAMPLE 34 cis-2-(Diphenylmethyl)-3-[(3-iodo-5-methyl)benzyloxy]-1-azabicyclo[2.2.2]octane cis-2-(Diphenylmethyl)-3-[(3-methyl-5-trimethylsilyl)benzyloxy]-1-azabicyclo[2.2.2]octane (Example 33) (150 mg) was dissolved in anhydrous methanol (5 ml) under nitrogen and cooled in an ice/methanol bath. Silver trifluoroacetate (148 mg) was added, and after 5 minutes iodine (81 mg) was added which produced a brown colouration. After 1 hour a yellow precipitate was formed. The solvent was removed in vacuo. The residue was taken up in ethyl acetate and filtered through celite. The filtrate was washed with sodium sulphite and dried (magnesium sulphate). The residue was purified by chromatography on silica using gradient solution from 100% dichloromethane to 5% methanol in dichloromethane to afford the title compound (100 mg) which was converted to the hydrochloride salt with methanolic hydrogen chloride; recrystallisation was from methanol-ethyl acetate: m.p. >250° C.

$\delta_H$ (360 MHz, CDCl$_3$) 1.22–1.34 (1H, m, NCH$_2$CHH), 1.44–1.56 (1H, m, NCH$_2$CHH), 1.58–1.71 (1H, m, NCH$_2$CHH), 1.74–1.88 (1H, m, NCH$_2$CHH), 2.06–2.14 (1H, m, NCH$_2$CH$_2$CH), 2.25 (3H, s, CH$_3$), 2.60–2.68 (1H, m, NCHH), 2.75–2.62 (2H, m, NCHH+NCHH), 3.08–3.17 (1H, m, NCHCH), 3.45–3.55 (2H, m, OCHH+CHO), 3.64–3.75 (1H, m, NCHCHPh$_2$), 4.01–4.04 (1H, d, J=11 Hz, OCHH), 4.45–4.49 (1H, d, J=12 Hz, CHPh$_2$), 6.67 (1H, s, Ar—H), 7.05–7.30 (11H, m, Ar—H), 7.42 (1H, s, Ar—H). MS (ACE) 524 (M++1, 10%); C$_{28}$H$_{31}$NOI. HCl requires: C, 60.06; H, 5.58; N, 2.50. Found: C, 60.21; H, 5.74; N, 2.44.

EXAMPLE 35 cis-2-(Diphenylmethyl)-3-[3-ethenylbenzyloxy]-1-azabicyclo[2.2.2]octane a) Methyl 3-ethylbenzoate

Methyl 3-iodobenzoate (13 g) and vinyl tributyltin (20 g) were dissolved in toluene (100 ml) and tetrakis(triphenylphosphine)palladium (0) (500 mg) added. The solution was heated at reflux with stirring under N$_2$ for 1 day. Potassium fluoride (3 g) in water (50 ml) was added and the reaction mixture was allowed to stir under N$_2$ for 15 minutes. The product was taken up in ethyl acetate and washed with water and then brine (×2). The organic extract was dried (MgSO$_4$) and evaporated in vacuo.

The residue was purified by gravity chromatography on silica using 10–30% dichloromethane in petrol 60–80 as eluant. The product was evaporated in vacuo:

$^1$H NMR (360 MHz, CDCl$_3$); δ 3.9 (3H, s, CH$_3$), 5.3 (1H, d, J=17 Hz, CH$_2$=CH), 5.8 (1H, d, J=17.5 Hz, CH$_2$=CH), 6.75 (1H, t, CH$_2$=CH—Ar), 7.4 (1H, t, ArH), 7.6 (1H, d, J=7.8 Hz, ArH), 7.9 (1H, d, J=10 Hz, ArH), 8.1 (1H, s, ArH).

b) 3-Ethenylbenzyl alcohol

Methyl-3-ethenylenzoate (6.9 g) was dissolved in tetrahydrofuran (100 ml) and stirred under N$_2$. Lithium aluminium hydride (1.0M in tetrahydrofuran, 26.5 ml) was added to the solution dropwise. The reaction mixture was allowed to stir under no starting material remained by tlc. Excess lithium aluminium hydride was destroyed by the addition of water (1 ml) dropwise, followed by 15% sodium hydroxide (1 ml) and water (3 ml) to afford a granular precipitate. Reaction mixture was then stirred with MgSO$_4$ for 1 hour, and then filtered through celite to remove inorganic matter. The solvent was evaporated in vacuo:

$^1$H NMR (250 MHz, CDCl$_3$); δ 2.4 (1H, s, OH), 4.6 (2H, s, CH$_2$OH), 5.2 (1H, d, CH$_2$=CH—Ar), 5.7 (1H, d, CH$_2$=CH—Ar), 6.7 (1H, dd, CH$_2$=CH—Ar), 7.15–7.4 (4H, m, ArH).

c) 3-Ethenylbenzyl chloride

3-Ethenylbenzyl alcohol (5.26 g) was dissolved in carbon tetrachloride (100 ml) and triphenylphosphine (10.2 g) added. The solution was refluxed overnight and then left to cool. A white precipitate formed which was filtered through celite. The filtrate was evaporated in vacuo to yield a crude product. The residue was purified by gravity chromatography on silica using 5% dichloromethane in petrol (60–80) as eluant. This yielded the pure product.

$^1$H NMR (250 MHz, CDCl$_3$); δ 4.6 (2H, s, CH$_2$—Cl), 5.3 (1H, d, CH$_2$=CH—Ar), 5.8 (1H, d, CH$_2$=CH—Ar), 6.7 (1H, m, CH$_2$=CH—Ar), 7.3 (3H, m, ArH), 7.4 (1H, s, ArH).

d) cis-2-(Diphenylmethyl)-3-[3-ethenylbenzyloxy]-1-azabicyclo[2.2.2] octane cis-2-(Diphenylmethyl)-1-azabicyclo[2.2.2]octan-3-ol (2 g) (Description 1) was dissolved in dimethoxyethane (50 mls) and potassium hexamethyldisilazide (13.6 ml, 0.5N in toluene) added while stirring under N$_2$. 3-Ethenylbenzyl chloride was added and the reaction allowed to stir for 1 hour. Excess dimethoxyethane was removed by evaporation in vacuo. The crude product was purified by gravity chromatography on alumina using petrol:ether, 70:30 as an eluant to remove any starting alcohol. The product was purified further on silica (Lobar) using 3% methanol in dichloromethane to afford the title compound, which was converted to the hydrochloride salt by treatment with methanolic hydrogen chloride: m.p. (ethyl acetate/methanol) 199°–201° C.

$^1$H NMR (360 MHz, CDCl$_3$) free base, δ 1.25–1.95 (4H, m, CH$_2$CH$_2$N+CH$_2$CH$_2$N), 2.15 (1H, d, J=4.6 Hz, bridgehead H), 2.75 (1H, t, CH$_2$N), 2.85 (2H, t, CH$_2$N), 3.15 (1H, m, CH$_2$N), 3.55 (1H, t, N—CH—CH—O), 3.6 (1H, d, J=11.0 Hz, O—CH$_2$—Ar), 3.75 (1H, m, N—CH—CH—O), 4.1 (1H, d, J=11 Hz, O—CH$_2$—Ar), 4.5 (1H, d, J=12 Hz, PhCHPh), 5.25 (1H, t, CH$_2$=CH—Ar), 5.75 (1H, d, J=18 Hz, CH$_2$=CH—Ar), 6.7 (1H, m, CH$_2$=CH—Ar), 6.85 (1H, d, J=7.5 Hz, ArH), 7.0 (1H, s, ArH), 7.1–7.3 (12H, m, ArH).

EXAMPLE 36 cis-2-(Diphenylmethyl)-3-[3-ethylbenzyloxy]-1-azabicyclo[2.2.2]octane cis-2-(Diphenylmethyl)-3-[3-ethylbenzyloxy]-1-azabicyclo[2.2.2]octane (Example 35 (300 mg) was dissolved in ethyl acetate (50 mls) and hydrogenated using platinum oxide catalyst (50 mg). After 3 hours, the hydrogenation was stopped, the catalyst filtered off, and the filtrate concentrated by evaporation in vacuo. The product was purified on silica (Lobar) using 3% methanol in dichloromethane to afford the title compound, which was converted to the hydrochloride salt by treatment with methanolic hydrogen chloride: m.p. (ethyl acetate/methanol) 223°-224° C.

$^1$H NMR (360 MHz, DMSO) free base, δ 1.15 (3H, t, J=7.5 Hz, CH$_3$), 1.75 (1H, q, CH$_2$CH$_2$N), 1.9 (3H, m, CH$_2$CH$_2$N), 2.5 (1H, s, bridgehead), 2.55 (2H, q, J=7.5 Hz, CH$_3$CH$_2$Ar), 3.05 (1H, t, CH$_2$N), 3.1 (1H, q, CH$_2$N), 3.25 (1H, t, CH$_2$N), 3.5 (1H, t, CH$_2$N), 3.55 (2H, d, J=11 Hz, O—CH$_2$—Ar), 3.8 (1H, t, NCH—CH—O), 4.15 (1H, d, J=11. Hz, O—CH$_2$—Ar), 4.65 (1H, d, J=12 Hz, PhCH—Ph), 4.95 (1H, m, NCH—CH—O), 6.75-7.6 (14H, m, ArH).

EXAMPLE 37 trans-3-(3,5-Dimethylbenzyloxy)-2-(diphenylmethyl)-1-azabicyclo[2.2.2]octane oxalate 2-(Diphenylmethyl)-1-azabicyclo[2.2.2]octan-3-ol (1.2 g), an 80:20 mixture of cis/trans isomers (Description 3), was dissolved in dimethoxyethane (50 ml, anhydrous). 18-Crown-6 (20 mg) was added to the stirred solution at room temperature. Potassium bis(trimethylsilyl)amide (0.5M in toluene, 9.8 ml) was added, and the solution was stirred for 30 min under nitrogen. A solution of 3,5-dimethylbenzyl bromide (0.98 g) in dimethoxyethane (2 ml) was added and the resulting mixture stirred for 1 hour. The mixture was diluted with dichloromethane and water. The organic layer was dried (MgSO$_4$) and evaporated. The residue was passed through a short column of alumina (grade III) using 1:1 hexane/ether as eluent; this removed unreacted alcohol. The cis and trans isomers of the product were separated by chromatography on silica (Lobar) using 5% methanol in dichloromethane as eluent. The trans isomer eluted first and was converted to the oxalate salt by treatment with oxalic acid in ether. The salt was recrystallised from isopropanol: m.p. 174°-178° C.

$^1$H NMR (360 MHz, D$_2$O) δ 1.87-2.12 (4H, m, 2×CH$_2$CH$_2$N), 2.28 (6H, s, CH$_3$), 2.48 (1H, s, CHCH$_2$N), 3.06 (1H, mc, CHHN), 3.34 (2H, mc, CH$_2$N), 3.48 (1H, m, CHHN), 3.64 (1H, d, J=10.5 Hz, OCHH), 3.68 (1H, mc, CHOH), 4.12 (1H, d, J=10.5 Hz, OCHH), 4.17 (1H, mc, —CHN), 4.32 (1H, d, J=12.5 Hz, CH(Ph)$_2$), 6.63 (2H, s, ArH, H2, H6), 7.02 (1H, s, ArH, H4), 7.34-7.59 (10H, 2×m, ArH).

Found: C, 72.77; H, 6.82; N, 2.80. C$_{29}$H$_{33}$NO.(COOH)$_2$.(H$_2$O)$_{0.5}$ requires: C, 72.91; H, 7.11; N, 2.79%.

EXAMPLE 38 trans-3-[3,5-Bis(trifluoromethyl)benzyloxy]-2-(diphenylmethyl)-1-azabicyclo[2.2.2]octane oxalate Following the method of Example 37, 2-(diphenylmethyl)-1-azabicyclo[2.2.2]octan-3-ol (1 g) (Description 3) and 3,5-bis(trifluoromethyl)benzyl bromide gave the title compound which was recrystallized from isopropanol: m.p. 202° C.

Found: C, 59.49; H, 4.85; N, 2.13. C$_{29}$H$_{27}$F$_6$NO.(COOH)$_2$ H$_2$O requires: C, 59.33; H, 4.97; N, 2.23%.

EXAMPLE 39 trans-3-(3,5-Dimethoxybenzyloxy)-2-(diphenylmethyl)-1-azabicyclo[2.2.2]octane oxalate Following the method of Example 37, 2-(diphenylmethyl)-1-azabicyclo[2.2.2]octan-3-ol (Description 3) and 3,5-dimethoxybenzyl chloride gave the title compound: m.p. 192°-194° C. (from IPA).

$^1$H NMR (DMSO-d$_6$) δ 1.58 (1H, m, CHHCH$_2$N), 1.82 (2H, m, CH$_2$CH$_2$N), 1.94 (1H, m, CHHCH$_2$N), 2.52 (1H, m, CHCH$_2$CH$_2$N), 2.81 (1H, m, CH$_2$CHHN), 3.0-3.2 (3H, m, CH$_2$CHHN+CH$_2$CH$_2$N), 3.37 (1H, m, —CHOCH$_2$), 3.48 (1H, d, J=11.0 Hz, OCHH), 3.71 (6H, s, OCH$_3$), 3.96 (1H, d, J=11.0 Hz, OCHH), 4.15 (1H, m, NCHCHPh$_2$), 4.26 (1H, d, J=11.0 Hz, CHPh$_2$), 6.19 (2H, d, J=2.0 Hz, ArH), 6.36 (1H, d, J=2.0 Hz, ArH), 7.19-7.32 (6H, m, ArH), 7.51-7.56 (4H, m, ArH). MS (CI+) 444 (40%).

Found: C, 68.82; H, 6.63; N, 2.61. Calcd. for C$_{29}$H$_{33}$NO$_3$. C$_2$O$_4$H$_2$: C, 69.06; H, 6.54; N, 2.58%.

EXAMPLE 40 trans-2-(Diphenylmethyl)-3-(3-phenoxybenzyloxy)-1-azabicyclo[2.2.2]octane oxalate Following the method of Example 37, 2-(diphenylmethyl)-1-azabicyclo[2.2.2]octan-3-ol (1 g) (Description 3) and 3-phenoxybenzyl chloride (0.9 g) gave the title compound: m.p. 178°-180° C. (IPA).

$^1$H NMR (DMSO-d$_6$) δ 1.62 (1H, m, CHHCH$_2$N), 1.87 (3H, m, CHHCH$_2$N+CH$_2$CH$_2$N), 2.31 (1H, m, CHCH$_2$CH$_2$N), 2.8-2.95 (1H, m, CH$_2$CHHN), 3.05-3.3 (3H, m, CH$_2$CHHN+CH$_2$CH$_2$N), 3.38 (1H, brs, CHOCH$_2$), 3.49 (1H, d, J=11.0 Hz, OCHH), 4.10 (1H, d, J=11.0 Hz, OCHH), 4.32 (1H, m) and 4.4-4.7 (1H, br m, NCHCHPh$_2$ and CHPh$_2$), 6.61 (1H, s, ArH), 6.71 (1H, d, J=8.0 Hz, ArH), 6.90 (1H, dd, J=10.0, 2.5 Hz, ArH), 7.00 (2H, d, J=8.0 Hz, ArH), 7.07-7.34 (8H, m, ArH). MS (CI+) 476 (100%).

Found: C, 74.19; H, 6.20; N, 2.44. Calcd. for C$_{33}$H$_{33}$NO$_2$ (C$_2$O$_4$H$_2$): C, 74.32; H, 6.24; N, 2.48%.

EXAMPLE 41 trans-2-(Diphenylmethyl)-3-(3-methoxy, 5-methylbenzyloxy)-1-azabicyclo[2.2.2]octane oxalate Following the method of Example 37, trans-2-(diphenylmethyl)-1-azabicyclo[2.2.2]octan-3-ol (Description 4) and 3-methoxy-5-methylbenzylbromide gave the title compound: m.p. 162°-164° C. (IPA).

$^1$H NMR (360 MHz, D$_2$O) δ 1.84 (2H, broad s) and 2.06 (2H, m, 2×CH$_2$ β to N), 2.28 (3H, s, CH$_3$), 2.43 (1H, broad s, CH at bridgehead), 3.07-3.09 (1H, m) and 3.28-3.33 (2H, m) and 3.46-3.49 (1H, m, 2×CH$_2$ α to N), 3.46-3.59 (1H, m, CHO), 3.49-3.55 (1H, d, J=11.5 Hz) and 4.03-4.06 (1H, d, J=11.5 Hz, CH$_2$O), 3.76 (3H, s, OCH$_3$), 3.95-4.01 (1H, m, CHN), 4.22-4.26 (1H, d, J=12.5 Hz, CHPh$_2$), 6.46 (1H, s), 6.48 (1H, s), 6.72 (1H, s) and 7.08-7.52 (10H, m, ArH). MS (FAB+) 428 (100%).

Found: C, 71.35; H, 6.76; N, 2.78. Calc. for C$_{29}$H$_{33}$NO$_2$.(CO$_2$H)$_2$. 0.25 (H$_2$O): C, 71.31; H, 6.85; N, 2.68.

EXAMPLE 42 trans-3-(3-Cyanobenzyloxy)-2-(diphenylmethyl)-1-azabicyclo[2.2.2]octane oxalate

Following the method of Example 37, trans-2-(diphenylmethyl)-1-azabicyclo[2.2.2]octan-3-ol (Description 4) and α-bromo-m-tolunitrile gave the title compound: m.p. 196°- 198° C. (IPA).

$^1$H NMR (360 MHz, D$_2$O) δ 1.87-2.14 (4H, m, 2×CH$_2$ β to N), 2.54 (H, m, CH at bridgehead), 3.01-3.09 (1H, m) and 3.30-3.48 (3H, m, 2×CH$_2$ α to N), 3.73 (1H, broad s, CHO), 3.79-3.83 (1H, d, J=11.5 Hz, CH of CH$_2$O), 4.19-4.23 (H, dd, J=12.5, 3.0 Hz, CHN), 4.30-4.34 (2H, d, J=11.5 Hz, CH of CH$_2$O and CHPh₂), 7.21-7.67 (14H, m, ArH). MS (FAB+) 409 (30%).

Found: C, 71.72; H, 5.92; N, 5.02. Calc. for C₂₈H₂₈N₂O. 1.1 (CO₂H): C, 71.40; H, 5.99; N, 5.51.

EXAMPLE 43

(+) trans-(2R,3S)-3-[3,5-Bis(trifluoromethyl)benzyloxy]-2-(diphenylmethyl)-1-azabicyclo[2.2.2]octane hydrochloride (−)-trans-2-(Diphenylmethyl)-1-azabicyclo[2.2.2]-octan-3-ol (Description 5, enantiomer A) (0.7 g) was dissolved in ethylene glycol dimethyl ether under N₂ at room temperature. 18-crown-6 (catalytic) was added followed by potassium bis(trimethylsilyl)amide (5.2 ml, 0.5N in toluene). After 10 minutes, 3,5-bis(trifluoromethyl)benzyl bromide (0.53 ml) was added and the mixture stirred for 2.5 hours; this was quenched with water and evaporated. The residue was partitioned between water and dichloromethane. The organics were separated, dried (Na₂SO₄) and evaporated to give a brown solid which was chromatographed through Grade III alumina eluted with 1:1 petrol:ether. A pure sample of the free base of the title compound (810 mg, 65%) was obtained by m.p.l.c. through a Lobar column eluted with 2.5% methanol in dichloromethane. It was converted to the salt on treatment with methanolic HCl and recrystallised from ethyl acetate/methanol: m.p. 246°-248° C.

$\delta_H$ (360 MHz, CDCl₃ free base) 1.85-2.14 (4H, m, 2×CH₂β to N); 2.50 (H, m, CH at bridgehead); 3.09 (H, m) and 3.37 (3H, m, 2×CH₂ α to N); 3.69 (H, broad s, CHO); 3.76-3.80 (H, d, J=11.9 Hz) and 4.36-4.39 (H, d, J=11.9 Hz, CH₂O); 4.25-4.29 (H, d, J=12.4 Hz, CHPh₂); 7.11-7.21 (3H, m); 7.36-7.54 (9H, m) and 7.92 (H, broad s, ArH).

Ether "A": C₂₉H₂₇F₆NO. HCl. H₂O requires: C, 60.68; H, 5.26; N, 2.44; Found: C, 60.55; H, 5.39; N, 2.50. [α]_D (MeOH, C=1)= +41.8°.

EXAMPLE 44

(−)-trans-(2S,3R)-3-[3,5-Bis(trifluoromethyl)benzyloxy]-2-(diphenylmethyl)-1-azabicyclo[2.2.2]octane hydrochloride According to the procedure described for Example 43 (+)-trans-2-(diphenylmethyl)-1-azabicyclo[2.2.2]octan-3-ol (Description 5, enantiomer B) afforded the title compound (60%): m.p. 246°-248° C.

C₂₉H₂₄F₆NO. HCl. H₂O requires: C, 60.68; H, 5.26; N, 2.44 Found: C, 60.62; H, 5.35; N, 2.50. [α]_D (MeOH, C=1)= −41.5°.

EXAMPLE 45 trans-(2R,3S)-3-(3,5-Dimethylbenzyloxy)-(diphenylmethyl)-1-azabicyclo[2.2.2]octan hydrochloride (−)-trans-2-(Diphenylmethyl)-1-azabicyclo[2.2.2]octan-3-ol (Description 5, enantiomer A) was reacted with 3,5-dimethylbenzyl bromide according to the procedure described in Example 43 affording the title compound: mp >250° C.

$\delta_H$ (360 MHz, CDCl₃ (free base)) 1.3 (1H, mc, CHH), 1.5 (1H, mc, CHH), 1.7 (1H, mc, CHH), 1.9 (1H, mc, CHH), 2.06 (1H, mc, CH bridgehead), 2.27 (6H, s, CH₃), 2.54 (1H, mc, CHHN), 2.94 (3H, mc, CHHN+CH₂N), 3.12 (1H, mc, CHOCH₂Ph), 3.49 (1H, d, J=14.5 Hz, OCHHPh), 3.55 (1H, mc, CHCHPh₂), 3.93 (1H, d, J=14.5 Hz, OCHHPh), 4.00 (1H, d, J=15 Hz, CHPh₂), 6.60 (2H, s, ArH), 6.86 (1H, s, ArH), 7.07-7.43 (10H, m, ArH).

EXAMPLE 46 trans-(2S,3R)-3-(3,5-Dimethylbenzyloxy)-2-(diphenylmethyl)-1-azabicyclo[2.2.2]octane hydrochloride (+)-trans-2-(Diphenylmethyl)-1-azabicyclo[2.2.2]octan-3-ol (Description 5, enantiomer B) was reacted with 3,5-dimethylbenzyl bromide according to the procedure described in Example 43 affording the title compound: m.p. 250° C.

$\delta_H$ (360 MHz, CDCl₃ free base) 1.3 (1H, mc, CHH), 1.5 (1H, mc, CHH), 1.7 (1H, mc, CHH), 1.9 (1H, mc, CHH), 2.06 (1H, mc, CH bridgehead), 2.27 (6H, s, CH₃), 2.54 (1H, mc, CHHN), 2.94 (3H, mc, CHHN+CH₂N), 3.12 (1H, mc, CHOCH₂Ph), 3.49 (1H, d, J=14.5 Hz, OCHHPh), 3.55 (1H, mc CHCHPh₂), 3.93 (1H, d, J=14.5 Hz, OCHHPh), 4.00 (1H, d, J=14.5 Hz, CHPh₂), 6.60 (2H, s, ArH), 6.86 (1H, s, ArH), 7.07-7.43 (10H, m, ArH). MS (FAB+) 412 (M⁺+1, 100%).

EXAMPLE 47 trans-3-(3,5-Dichlorobenzyloxy)-2-(diphenylmethyl)-1-azabicyclo[2.2.2]octane oxalate trans-2-(Diphenylmethyl)-1-azabicyclo[2.2.2]octan-3-ol (Description 4) (0.8 g) was suspended in dimethoxyethane (25 ml) under nitrogen. Potassium bis(trimethylsilyl)amide (6.5 ml, 0.5M in toluene) was added to the stirred suspension affording a clear orange solution. After 1 hour at room temperature 3,5-dichlorobenzyl chloride was added in one portion and the mixture resulting was stirred for 2 h. The solvent was removed in vacuo and the residue was suspended in dichloromethane and washed with water and brine; the organic layer was dried (MgSO₄) and evaporated. This was purified by chromatography on alumina III using 70:30 hexane:petrol as eluent. Further purification was effected by medium pressure chromatography on silica using 3% methanol in dichloromethane as eluent. This afforded the title compound 0.6 g (50%) as a white crystalline solid. This was converted to the oxalate salt using oxalic acid in ether. Recrystallisation from isopropanol:DCM furnished the salt: m.p. 208°-210° C.

$\delta_H$ (360 MHz, DMSO-d₆) 1.5-1.6 (1H, m, CHHCH₂N), 1.72-2.0 (3H, m, CHHCH₂N+CH₂CH₂N), 2.22-2.3 (1H, m, CHCH₂CH₂N), 2.69-2.82 (1H, m, CHHN), 2.99-3.26 (3H, m, CHB+CH₂N), 3.41 (1H, mc, CHOCH₂Ph), 3.57 (1H, d, J=12 Hz, OCHHPh), 4.01-4.08 (1H, m, N+CHCHPh₂), 4.18 (1H, d, J=12 Hz, OCHHPh), 4.24 (1H, d, J=12.5 Hz, CHPh₂), 6.94-7.6 (13H, m, ArH). MS (ACE, CI+) 452 (M⁺+1, 100%).

EXAMPLE 48 cis-(exo)-3-(3,5-Dimethylbenzyloxy)-2-(diphenylhydroxymethyl)-1-azabicyclo[2.2.1]heptane oxalate (a) 2-(Diphenylhydroxymethyl)-1-azabicyclo[2.2.1]heptan-3-one To a stirred mixture of 1-azabicyclo[2.2.1]heptan-3-one hydrochloride (1.06 g) and benzophenone (1.82 g) in dry THF (5 ml) at −78° C. under argon was added a solution of lithium bis(trimethylsilyl)amide (18 ml, 1.0M in THF). The solution was stirred at −78° C. for 1 h, allowed to warm to room temperature and stirred for 48 h. The mixture was poured onto water and extracted with dichloromethane (×4). The combined extracts were dried (Na$_2$SO$_4$), evaporated in vacuo, and the residue was purified by chromatography on silica using a gradient elution of 10–30% ethyl acetate in dichloromethane to afford the title compound as a white solid:

$^1$H NMR (360 MHz, CDCl$_3$) 1.8–1.9 (1H, m, CHHCH$_2$N), 2.0–2.15 (1H, m, CHHCH$_2$N), 2.28 (2H, brs, CH$_2$N), 2.61 (1H, d, J=4.5 Hz, CHCH$_2$N), 2.9–3.0 (1H, m, CHHN), 3.0–3.2 (1H, m, CHHN), 3.70 (1H, s, CHN), 5.5 (1H, brs, Ph$_2$COH), 7.1–7.6 (10H, m, ArH).

(b)
2-(Diphenylhydroxymethyl)-1-azabicyclo[2.2.1]heptan-3-ol 2-(Diphenylhydroxymethyl)-1-azabicyclo[2.2.1]heptan-3-one (210 mg) was dissolved in THF (5 ml) at −78° C. under argon. Lithium aluminium hydride (3 ml, 1.0M in ether) was added and the mixture stirred at −78° C. for 30 min, and then warmed to room temperature whereupon the reaction mixture became homogeneous. Water (0.1 ml) was added followed by sodium hydroxide (0.35 ml, 3N) and water (0.35 ml) affording a granular precipitate. Solid sodium sulphate was added, the mixture was filtered and the filtrate evaporated. The resulting diol was used without further purification.

(c)
cis-(exo)-3-(3,5-Dimethylbenzyloxy)-2-(diphenylhydroxymethyl)-1-azabicyclo[2.2.1]heptane oxalate A solution of the crude diol described in (b) was dissolved in dry dimethoxyethane (3 ml) under argon. This was treated with potassium bis(trimethylsilyl)amide (5 ml, 0.5M in toluene), followed by 3,5-dimethylbenzyl bromide (0.47 g) and the mixture was stirred for 1 h. The solvents were evaporated in vacuo and the residue partitioned between aqueous ammonium chloride and dichloromethane. The organic layer was dried (Na$_2$SO$_4$) and evaporated. The residue was purified by chromatography on alumina (grade III) using 50% dichloromethane in ethyl acetate as eluant and then neat isopropanol. The product was recrystallized from petrol. The product was isolated as its oxalate salt by treatment of a solution of the free base with ethereal oxalic acid: m.p. 188°–190° C.

$^1$H NMR (360 MHz, D$_2$O) δ 1.73–1.77 (1H, m, CHHCH$_2$N), 2.20 (6H, s, CH$_3$), 2.2 (1H, m, CHHCH$_2$N), 3.1–3.3 (4H, m, CH$_2$N+CHCH$_2$N+CHCHHN), 3.93 (1H, d, J=10.5 Hz, OCHH), 3.9 (1H, m, CHCHHN), 4.13 (1H, d, J=10.5 Hz, OCHH), 4.46 (1H, d, J=6.0 Hz, CHO), 5.07 (1H, d, J=6.0 Hz, CHN), 6.38 (2H, s, ArH), 7.00 (1H, s, ArH), 7.3–7.65 (10H, m, ArH). MS (FAB+) 414 (M+, 100%).

C$_{28}$H$_{31}$NO$_2$. 1.1 (COOH)$_2$.H$_2$O requires: C, 68.36; H, 6.69; N, 2.64. Found: C, 68.08; H, 6.84; N, 2.64%.

EXAMPLE 49 cis-3-(3-Carbomethoxybenzyloxy)-2-(diphenylmethyl)-1-azabicyclo[2.2.2]octane oxalate cis-3-(3-Cyanobenzyloxy)-2-(diphenylmethyl)-1-azabicyclo[2.2.2]octane (Example 11) (500 mg) was suspended in concentrated hydrochloric acid (40 ml) and was heated at reflux for 2 h. Methanol was added to increase solubility and the solution heated at reflux overnight. The solution was evaporated to dryness and then dissolved in anhydrous methanolic hydrogen chloride and stirred overnight. The solvent was evaporated and the free base was liberated by treatment of the residue with aqueous sodium bicarbonate. This was extracted into dichloromethane, dried (MgSO$_4$) and evaporated. The residue was purified on silica (MPLC, Lobar) using 5%, methanol in dichloromethane. This afforded the product as a white crystalline solid which was converted to its oxalate salt by treatment of ethereal oxalic acid (1.1 equiv). This was recrystallized from isopropanol: m.p. 209°–210° C.

MS (FAB+) 422 (M++1); C$_{29}$H$_{31}$NO$_3$.1.1 (COOH)$_2$ requires: C, 69.32; H, 6.19; N, 2.59. Found: C, 69.48; H, 5.91; N, 2.96%.

EXAMPLE 50 cis-3-[3,5-Bis(trifluoromethyl)benzyloxy]-2-(diphenylmethyl)-1-methyl-1-azabicyclo[2.2.2]octane chloride The compound of Example 5 (500 mg) was dissolved in acetone (3 ml) and methyl iodide was added until tlc indicated no starting material was present. The solution was diluted with ether to afford a white crystalline solid which was filtered and dried (0.58 g). A portion was converted to the chloride salt by passing an acetonitrile/water solution of the iodide through Dowex (Cl$^-$ form) to afford the title compound: m.p. >250° C.

$^1$H (360 MHz, CH$_3$CN-d$_3$) δ 1.8–2.1 (3H, m, NCH$_2$CHH+NCH$_2$CH$_2$), 2.48 (3H, s, N+CH$_3$), 2.5 (1H, m, NCH$_2$CHH), 2.65 (1H, mc, NCH$_2$CH$_2$CH), 3.09 (1H, d, J=12 Hz, OCHHAr), 3.2–3.3 (1H, m, NCHH), 3.5–3.6 (1H, m, NCHH), 3.8–3.9 (1H, m, NCHH), 4.0–4.1 (1H, m, NCHH), 4.16 (1H, t, NCHCHO), 4.34 (1H, d, J=12 Hz, OCHHAr), 4.75 (1H, d, J=12 Hz, Ph$_2$CH), 5.70 (1H, m, N+CHCHPh$_2$), 7.0–8.0 (13H, m, ArH). MS (FAB+) 534 (M+H)+ 100%.

EXAMPLE 51

2-[(2-Chlorophenyl)phenylmethyl]-3-(3,5-dimethylbenzyloxy)-1-azabicyclo[2.2.2]octane hydrochloride a)
2-(2-Chlorobenzylidene)-1-azabicyclo[2.2.2]octan-3-one 1-Azabicyclo[2.2.2]octan-3-one (3.86 g) was heated at reflux with 2-chlorobenzaldehyde (8.33 ml), potassium hydroxide (0.4 g) and methanol (60 ml) under nitrogen for 2.5 hours. The volatiles were removed in vacuo and the residue washed with sodium hydrogen carbonate. This was extracted (×4) with dichloromethane. The organic layer was washed with water and dried (MgSO$_4$). The dichloromethane was removed in vacuo and the residue recrystallised from methanol-dichloromethane, to afford the title compound as yellow crystals:

$^1$H NMR (360 MHz, CDCl$_3$) 2.01–2.07 (4H, m, CH$_2$+CH$_2$), 2.64–2.68 (1H, m, CH bridgehead), 2.92–3.04 (2H, m, CH$_2$), 3.10–3.20 (2H, m, CH$_2$), 7.19–7.29 (2H, m, Ar—H), 7.36–7.42 (1H, m, Ar—H), 7.48 (1H, s, NC=CHPh), 8.45–8.48 (1H, m, Ar—H). MS (ACE 248 (M++1, 100%).

b)
2-[(2-Chlorophenyl)phenylmethyl]-1-azabicyclo[2.2.2]octan-3-one 2-(2-Chlorobenzylidene)-1-azabicyclo[2.2.2]octan-3-one (3 g) was dissolved in toluene (30 ml) and placed in a dropping funnel. Phenylmagnesium bromide was dissolved in toluene (15 ml) and stirred under nitrogen.

This was cooled in an ice/water bath and the benzylidene solution was added dropwise. After 3 hrs the reaction was quenched with ammonium chloride solution and the aqueous layer extracted with dichloromethane (×4); this was combined with the original toluene layer and dried (MgSO$_4$). The solvent was removed in vacuo and the residue purified by chromatography on silica eluting with 1:1 hexane:diethyl ether which afforded the title compound as a 2:1 mixture of its diastereoisomers:

$^1$H NMR (250 MHz, CDCl$_3$) 1.84–2.21 (4H, m, CH$_2$), 2.38–2.48 (1H, m, CH bridgehead), 2.56–2.86 (2H, m, CH$_2$), 2.92–3.18 (2H, m, CH$_2$), 3.88–3.92 (1H, d, J=10 Hz, NCHCHPh$_2$ diastereoisomer A), 3.97–4.01 (1H, d, J=10 Hz, NCHCHPh$_2$ diastereoisomer B), 4.82–4.87 (1H, d, J=12 Hz, CHPh diastereoisomer B), 5.17–5.22 (1H, d, J=12 Hz, CHPh$_2$ diastereoisomer A), 7.06–7.63 (9H, m, Ar—H).

c)
2-[(2-Chlorophenyl)phenylmethyl]-1-azabicyclo[2.2.2]octan-3-ol

The ketone described in (b) (2.51 g) was dissolved in THF (30 ml) and stirred under nitrogen at −78° C. and lithium aluminium hydride (15.42 ml 1.0M in THF) was added dropwise. After 3 hrs the excess hydride was destroyed by a Fieser work-up (0.6 ml H$_2$O added carefully followed by 0.6 ml 15% NaOH and 1.8 ml H$_2$O). The insoluble aluminium salts formed were removed by filtration and the residue was concentrated in vacuo to afford the title compound as a white solid:

$^1$H NMR (250 MHz, CDCl$_3$) mixture of isomers: 1.16–1.18 (1H, d, J=5 Hz, CHOH), 1.19–1.76 (4H, m, NCH$_2$CH$_2$+NCH$_2$CH$_2$), 1.82–2.06 (1H, m, bridgehead), 2.62–2.88 (3H, m, NCH$_2$+NCHH), 3.16–3.35 (1H, m, NCHH), 3.56–3.75 (1H, m, CHOH), 3.84–4.02 (1H, m, NCH), 5.00–5.05 (1H, d, J=12 Hz, CHPhPh, Diastereoisomer A), 5.23–5.28 (1H, d, J=12 Hz, CHPhPh, Diastereoisomer B), 6.96–7.60 (9H, m, Ar—H).

d)
cis-2-[(2-Chlorophenyl)phenylmethyl]3-[3,5-dimethylbenzyloxy]-1-azabicyclo[2.2.2]octane hydrochloride The alcohol of (c) (1 g) was dissolved in anhydrous dimethoxyethane (25 ml) and stirred under nitrogen. Potassium bis(trimethylsilyl)amide (7.3 ml, 0.5M in toluene) was added dropwise to the stirred solution to afford a light brown milky precipitate. After stirring for 1 hour, 3,5-dimethylbenzylbromide (0.91 g) was added and the resulting mixture was stirred for 2 hrs. The solvent was removed in vacuo and the residue dispersed in water and extracted with dichloromethane. The combined organic layers were dried (MgSO$_4$) and concentrated in vacuo to afford a brown oil. This residue was purified by chromatography on alumina (III) using hexane/ether (70:50) as eluent. This afforded 0.47 g of the ether which was further purified by medium pressure chromatography on silica (Lobar) using 4% methanol in dichloromethane as eluent to give 0.4 g of clear oil, yield=31%. This was converted to the hydrochloride salt with methanolic hydrogen chloride; recrystallisation from methanol/ethyl acetate afforded the title compound.

$^1$H NMR (250 MHz, CDCl$_3$) free base as a mixture of isomers 2:1 ratio 1.18–1.35 (1H, m, NCH$_2$CHH), 1.38–1.94 (3H, m, NCH$_2$CHH+NCH$_2$CH$_2$), 2.07–2.16 (1H, m, CH bridgehead), 2.27 (6H, s, 2CH$_3$ isomer A), 2.29 (6H, s, 2CH$_3$ isomer B), 2.57–2.85 (3H, m, NCH$_2$+NCHH), 3.13–3.32 (1H, m, NCHH), 3.47–3.81 (3H, m, NCH+CHO+CHOCHH), 4.04–4.08 (1H, d, J=10 Hz, CHOCHH isomer A), 4.08–4.12 (1H, d, J=10 Hz, CHOCHH isomer B), 4.97–5.02 (1H, d, J=12 Hz, CHPhC$_6$H$_4$Cl isomer A), 5.25–5.30 (1H, d, J=12 Hz, CH PhC$_6$H$_4$Cl isomer B), 6.52 (1H, s, ortho H isomer A), 6.58 (1H, s, ortho H isomer B), 6.83–6.90 (1H, m, para H), 6.96–7.56 (9H, m, Ar—H).

EXAMPLE 52 cis-3-(3-Aminobenzyloxy)-2-(diphenylmethyl)1-azabicyclo[2.2.2]octane

The compound of Example 1 was converted to the free base and dissolved in ethyl acetate. This was hydrogenated over platinum oxide catalyst at 40 psi for ten minutes. The catalyst was removed by filtration and the filtrate concentrated in vacuo to afford the title compound as a white crystalline solid.

$\delta_H$ (250 MHz, CDCl$_3$ (free base)) 1.18–1.94 (4H, m, NCH$_2$CH$_2$+NCH$_2$CH$_2$), 2.00–2.16 (1H, m, CH bridgehead), 2.54–2.86 (3H, m, NCH$_2$+NCHH), 3.06–3.25 (1H, m, NCHH), 3.44–3.77 (3H, m, CHO+NCHCHPh$_2$+OCHH), 4.07–4.11 (1H, d, J=10 Hz, OCHH), 4.51–4.56 (1H, d, J=12.5 Hz, CHPh$_2$), 6.03 (1H, s, ArH ortho), 6.36 (1H, d, J=10 Hz, ArH), 6.54 (1H, d, J=10 Hz, ArH), 6.96–7.44 (11H, m, ArH).

We claim:

1. A compound of formula (I), or salts or prodrugs thereof:

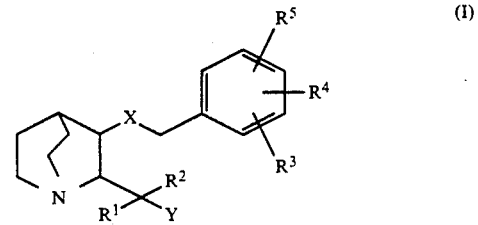

wherein

X is selected from oxa and thia;

Y is selected from H and hydroxy;

R$^1$ and R$^2$ are independently selected from phenyl and thienyl, either of which groups may be optionally substituted by a substituent selected from halo and trifluoromethyl;

R$^3$, R$^4$ and R$^5$ are independently selected from the group consisting of H, C$_{1-6}$ alkyl, C$_{2-6}$ alkenyl, C$_{2-6}$ alkynyl, halo, cyano, nitro, trifluoromethyl, trimethylsilyl, —OR$^a$, SCH$_3$, SOCH$_3$, SO$_2$CH$_3$, —NR$^a$R$^b$, —NR$^a$COR$^b$, —NR$^a$CO$_2$R$^b$, —CO$_2$R$^a$ and —CONR$^a$R$^b$; and R$^a$ and R$^b$ are independently selected from the group consisting of H, C$_{1-6}$ alkyl, phenyl and trifluoromethyl.

2. The compound as claimed in claim 1, wherein Y is selected from H and hydroxy; R$^3$, R$^4$ and R$^5$ are independently selected from the group consisting of H, C$_{1-6}$ alkyl, C$_{2-6}$ alkenyl, C$_{2-6}$ alkynyl, halo, cyano, nitro, trifluoromethyl, —OR$^a$, —NR$^a$R$^b$, —NR$^a$COR$^b$, —NR$^a$CO$_2$R$^b$, —CO$_2$R$^a$, —CONR$^a$R$^b$, SCH$_3$ and SO$_2$CH$_3$ where R$^a$ and R$^b$ are independently selected from H and C$_{1-6}$ alkyl; and when Y is H; R$^3$, R$^4$ and R$^5$ may also independently represent SOCH$_3$.

3. The compound as claimed in claim 1 wherein Y is H.

4. The compound a claimed in claim 3 wherein $R^3$, $R^4$ and $R^5$ are independently selected from the group consisting of H, $C_{1-6}$ alkyl, $C_{2-6}$ alkenyl, $C_{2-6}$ alkynyl, halo, cyano, nitro, trifluoromethyl, —$OR^a$, —$NR^aR^b$, —$NR^aCOR^b$, —$NR^aCO_2R^b$, —$CO_2R^a$ and —$CONR^aR^b$; and $R^a$ and $R^b$ are independently selected from H and $C_{1-6}$ alkyl.

5. The compound as claimed in claim 1 wherein
Y is H;
$R^3$, $R^4$ and $R^5$ are independently selected from the group consisting of H, $C_{1-6}$alkyl, $C_{2-6}$alkenyl, halo, cyano, nitro, trifluoromethyl, —$OR^a$, $NR^aR^b$ and —$CO_2R^a$; and $R^a$ and $R^b$ are independently selected from H and $C_{1-6}$alkyl.

6. The compound according to claim 1 selected from the group consisting:
trans-3-(3,5-dimethylbenzyloxy)-2-(diphenylmethyl)-1-azabicyclo[2.2.2]octane;
trans-3-[3,5-bis(trifluoromethyl)benzyloxy]-2-(diphenylmethyl)-1-azabicyclo[2.2.2]octane;
trans-3-(3,5-dimethoxybenzyloxy)-2-(diphenylmethyl)-1-azabicyclo[2.2.2]octane;
trans-2-(diphenylmethyl)-3-(3-phenoxybenzyloxy)-1-azabicyclo[2.2.2]octane;
trans-2-(diphenylmethyl)-3-(3-methoxy,5-methylbenzyloxy)-1-azabicyclo[2.2.2]octane;
trans-3-(3-cyanobenzyloxy)-2-(diphenylmethyl)-1-azabicyclo[2.2.2]octane;
trans-(2R,3S)-3-[3,5-bis(trifluoromethyl)benzyloxy]-2-(diphenylmethyl)-1-azabicyclo[2.2.2]octane;
trans-(2R,3S)-3-(3,5-dimethylbenzyloxy)-2-(diphenylmethyl)-1-azabicyclo[2.2.2]octane;
trans-3-(3,5-dichlorobenzyloxy)-2-(diphenylmethyl)-1-azabicyclo[2.2.2]octane;
cis-2-(diphenylmethyl)-3-(3-nitrobenzyloxy)-1-azabicyclo[2.2.2]octane;
cis-2-(diphenylmethyl)-3-[2-(trifluoromethyl)benzyloxy]-1-azabicyclo[2.2.2]octane;
cis-3-(2-chlorobenzyloxy)-2-(diphenylmethyl)-1-azabicyclo[2.2.2]octane;
cis-3-(3-chlorobenzyloxy)-2-(diphenylmethyl)-1-azabicyclo[2.2.2]octane;
cis-3-[3,5-bis(trifluoromethyl)benzyloxy]-2-(diphenylmethyl)-1-azabicyclo[2.2.2]octane;
cis-2-(diphenylmethyl)-3-[4-(trifluoromethyl)benzyloxy]-1-azabicyclo[2.2.2]octane;
cis-3-benzyloxy-2-(diphenylmethyl)-1-azabicyclo[2.2.2]octane;
cis-3-(3,5-difluorobenzyloxy)-2-(diphenylmethyl)-1-azabicyclo[2.2.2]octane;
cis-2-(diphenylmethyl)-3-(4-methoxybenzyloxy)-1-azabicyclo[2.2.2]octane;
cis-2-(diphenylmethyl)-3-(3-methoxybenzyloxy)-1-azabicyclo[2.2.2]octane;
cis-3-(2-cyanobenzyloxy)-2-(diphenylmethyl)-1-azabicyclo[2.2.2]octane;
cis-3-(3-cyanobenzyloxy)-2-(diphenylmethyl)-1-azabicyclo[2.2.2]octane;
cis-2-(diphenylmethyl)-3-(3-trifluoromethylbenzyloxy)-1-azabicyclo[2.2.2]octane;
cis-3-(3,5-dimethylbenzyloxy)-2-diphenylmethyl-1-azabicyclo[2.2.2]octane;
cis-3-(2,5-difluorobenzyloxy)-2-diphenylmethyl-1-azabicyclo[2.2.2]octane;
cis-2-(diphenylmethyl)-3-(3-fluorobenzyloxy)-1-azabicyclo[2.2.2]octane;
cis-2-diphenylmethyl-3-(2-fluorobenzyloxy)-1-azabicyclo[2.2.2]octane;
cis-3-(2,5-dimethylbenzyloxy)-2-(diphenylmethyl)-1-azabicyclo[2.2.2]octane;
cis-2-diphenylmethyl-3-(3-methylbenzyloxy)-1-azabicyclo[2.2.2]octane;
cis-3-(4-chlorobenzyloxy)-2-diphenylmethyl-1-azabicyclo[2.2.2]octane;
cis-2-(diphenylmethyl)-3-(4-methylbenzyloxy)-1-azabicyclo[2.2.2]octane;
cis-3-(3,4-dimethylbenzyloxy)-2-(diphenylmethyl)-1-azabicyclo[2.2.2]octane;
cis-2-(diphenylmethyl)-3-(4-fluorobenzyloxy)-1-azabicyclo[2.2.2]octane;
cis-2-(diphenylmethyl)-3-(2-methylbenzyloxy)-1-azabicyclo[2.2.2]octane;
cis-3-(4-cyanobenzyloxy)-2-(diphenylmethyl)-1-azabicyclo[2.2.2]octane;
cis-3-(2-bromobenzyloxy)-2-(diphenylmethyl)-1-azabicyclo[2.2.2]octane;
cis-3-(3,5-dichlorobenzyloxy)-2-diphenylmethyl)-1-azabicyclo[2.2.2]octane;
cis-3-(3,5-dimethoxybenzyloxy)-2-(diphenylmethyl)-1-azabicyclo[2.2.2]octane;
cis-2-(diphenylmethyl)-3-(3-methoxy,5-methylbenzyloxy)-1-azabicyclo[2.2.2]octane;
cis-2-(diphenylmethyl)-3-(3-phenoxybenzyloxy)-1-azabicyclo[2.2.2]octane;
cis-(2S,3S)-3-[3,5-bis(trifluoromethyl)benzyloxy]-2-(diphenylmethyl)-1-azabicyclo[2.2.2]octane;
cis-2-(diphenylmethyl)-3-[(3-methyl-5-trimethylsilyl)benzyloxy]-1-azabicyclo[2.2.2]octane;
cis-2-(diphenylmethyl)-3-[(3-methyl-5-iodo)benzyloxy]-1-azabicyclo[2.2.2]octane;
cis-2-(diphenylmethyl)-3-[3-ethenylbenzyloxy]-1-azabicyclo[2.2.2]octane;
cis-2-(diphenylmethyl)-3-[3-ethylbenzyloxy]-1-azabicyclo[2.2.2]octane;
cis-3-(3-carbomethoxybenzyloxy)-2-(diphenylmethyl)-1-azabicyclo[2.2.2]octane;
cis-3-[3,5-bis(trifluoromethyl)benzyloxy]-2-(diphenylmethyl)-1-methyl-1-azabicyclo[2.2.2]octane;
2-[(2-chlorophenyl)phenylmethyl]-3-(3,5-dimethylbenzyloxy)-1-azabicyclo[2.2.2]octane;
cis-3-(3-aminobenzyloxy)-2-(diphenylmethyl)-1-azabicyclo[2.2.2]octane;
or salt or prodrug thereof.

7. The compound as claimed in claim 1 wherein the sterochemical configuration at the 3-position of the azabicycle is (S).

8. A compound as claimed in claim 1 wherein
$R^1$ and $R^2$ are independently selected from the group consisting of phenyl, optionally substituted by halo;
$R^3$, $R^4$ and $R^5$ are independently selected from the group consisting of H, $C_{1-6}$alkyl, $C_{2-6}$alkenyl, halo, cyano, nitro, trifluoromethyl, trimethylsilyl, —$OR^a$, —$NR^aR^b$ and —$CO_2R^a$; and $R^a$ and $R^b$ are independently selected from the group consisting of H, $C_{1-6}$alkyl and phenyl.

9. A pharmaceutical composition comprising a compound as claimed in claim 1 in association with a pharmaceutically acceptable carrier thereof.

10. A method for the treatment of a physiological disorder associated with an excess of tachykinins, which method comprises administration to a patient in need thereof of a tachykinin-reducing amount of a compound according to claim 1.

11. The method according to claim 10 for the treatment of pain.

* * * * *